(12) United States Patent
Tao et al.

(10) Patent No.: US 10,143,401 B2
(45) Date of Patent: Dec. 4, 2018

(54) METABOLIC ANALYZER

(75) Inventors: Nongjian Tao, Scottsdale, AZ (US); Erica Forzani, Mesa, AZ (US)

(73) Assignee: ARIZONA BOARD OF REGENTS ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1060 days.

(21) Appl. No.: 13/493,552

(22) Filed: Jun. 11, 2012

(65) Prior Publication Data

US 2013/0150746 A1  Jun. 13, 2013

Related U.S. Application Data

(60) Provisional application No. 61/514,194, filed on Aug. 2, 2011, provisional application No. 61/496,483, filed on Jun. 13, 2011.

(51) Int. Cl.
*A61B 5/08* (2006.01)
*A61B 5/083* (2006.01)
*G06Q 50/22* (2018.01)

(52) U.S. Cl.
CPC .......... *A61B 5/0833* (2013.01); *A61B 5/0836* (2013.01); *G06Q 50/22* (2013.01);
(Continued)

(58) Field of Classification Search
CPC ........... A24F 47/00; A61B 5/08; A61B 5/082; A61B 5/083; A61B 5/0833; A61B 5/0836; G01N 33/4972
(Continued)

(56) References Cited

U.S. PATENT DOCUMENTS

| 5,050,656 | A | | 9/1991 | Ho |
| 5,237,631 | A | * | 8/1993 | Gavish ................ G01N 21/643 385/12 |

(Continued)

FOREIGN PATENT DOCUMENTS

| WO | WO2007072395 A2 | 6/2007 |
| WO | WO2007072395 A3 | 6/2007 |
| WO | WO2009058366 A1 | 5/2009 |

OTHER PUBLICATIONS

Arthur E. Colvin, Jr, et al. , A Novel Solid-State Oxygen Sensor, 1996, Johns Hopkins APL Technical Digest, vol. 17, pp. 377-385.*

(Continued)

*Primary Examiner* — Puya Agahi
(74) *Attorney, Agent, or Firm* — George A. Leone; Citadel Patent Law

(57) ABSTRACT

A method for weight and/or fitness management using a metabolic analyzer that measures metabolic data including oxygen and carbon dioxide. The metabolic analyzer includes integrated collection-detection sensors with for high efficiency and collection, high specificity and simultaneous detection of at least two metabolic signatures, including at least oxygen and carbon dioxide, in breath via a porous membrane with high density of sensing binding sites, where the porous membrane includes sensing materials such that the sensing binding sites are specific to the metabolic signatures, and change colors upon interactions with the metabolic signatures. Weight of the subject is measured using a weight measurement device and a recommendation for food intake and/or physical activity is based on at least the readings of the metabolic analyzer and weight of the subject.

17 Claims, 15 Drawing Sheets

(52) U.S. Cl.
CPC .............. *A61B 5/08* (2013.01); *A61B 5/083* (2013.01); *Y02P 90/84* (2015.11); *Y02P 90/845* (2015.11)

(58) Field of Classification Search
USPC ....... 600/301, 529, 531, 532, 538, 540, 543; 128/921
See application file for complete search history.

(56) References Cited

U.S. PATENT DOCUMENTS

| | | | |
|---|---|---|---|
| 5,839,901 | A | 11/1998 | Karkanen |
| 6,454,723 | B1 | 9/2002 | Montagnino |
| 6,478,736 | B1* | 11/2002 | Mault .......................... 600/300 |
| 6,492,182 | B1* | 12/2002 | Bright .................. G01N 33/542 422/534 |
| 6,790,178 | B1* | 9/2004 | Mault et al. .................. 600/300 |
| 6,989,246 | B2 | 1/2006 | Yeh |
| 7,108,659 | B2 | 9/2006 | Ross et al. |
| 7,364,551 | B2 | 4/2008 | Allen et al. |
| 2002/0143267 | A1 | 10/2002 | Montagnino |
| 2002/0156351 | A1 | 10/2002 | Sagel |
| 2003/0208133 | A1 | 11/2003 | Mault |
| 2004/0236244 | A1* | 11/2004 | Allen et al. ................... 600/532 |
| 2005/0084921 | A1 | 4/2005 | Cranley et al. |
| 2005/0234742 | A1* | 10/2005 | Hodgdon ......................... 705/2 |
| 2006/0259323 | A1 | 11/2006 | Chan |
| 2007/0093725 | A1 | 4/2007 | Shaw |
| 2007/0229818 | A1 | 10/2007 | Duan et al. |
| 2008/0004542 | A1 | 1/2008 | Allen et al. |
| 2008/0119751 | A1* | 5/2008 | Flanagan ...................... 600/531 |
| 2008/0220984 | A1* | 9/2008 | Bright et al. .................. 506/12 |
| 2009/0049890 | A1 | 2/2009 | Zhong et al. |
| 2009/0054799 | A1* | 2/2009 | Vrtis et al. .................... 600/532 |
| 2009/0127100 | A1 | 5/2009 | Fleischer et al. |
| 2009/0131814 | A1 | 5/2009 | Thompson |
| 2009/0227887 | A1 | 9/2009 | Howard et al. |
| 2010/0049004 | A1 | 2/2010 | Edman et al. |
| 2011/0143322 | A1 | 6/2011 | Tsang |
| 2011/0247638 | A1* | 10/2011 | Ayala ........................... 131/270 |

OTHER PUBLICATIONS

Y.Y. Kievsky et al., Dynamics of Molecular Diffusion of Rhodamine 6G in silica, The Journal of Chemical Physics, 128, Doi: 10.1063/1.2908875.*
Body Mass Index—BMI, World Health Organization, p. 1.*
Stephanie Wilson, Body Mass Index, howstuffworks, Nov. 7, 2007, p. 1.*
Jaeger, "Oxycon Mobile: Wireless portable ergospirometry system," Product Description found on Viasys Healthcare webpage, Oct. 2008.
Kemeta, "Kemeta Breath Analyzer for Fat Metabolism," Kemeta Technology, Oct. 2010.
Kunze, Klaudia, et al., "Sensor Warns Patients in Advance of Asthma Attack," Siemens Innovation News, Feb. 2011.
Jaeger, "Oxycon Pro, Product Description," Intra Medic website (translated to English).
American Dietetic Association, "Adult Weight Management Evidence-Based Nutrition Practice Guideline," 2013.
American Dietetic Association, "Pediatric Weight Management Evidence-Based Nutrition Practice Guideline," 2013.
Elliot, D.L., et al., "Sustained Decrement in Resting Metabolic Rate Following Weight Loss," Clin. Res., 1987, p. 365A, vol. 35, No. 3.
Elliot, D.L., et al., "Sustained depression of the resting metabolic rate after massive weight loss," Am. J. Clin. Nut., 1989, pp. 93-96, vol. 49.
Heshka, Stanley, et al., "Weight loss and change in resting metabolic rate," Am. J. Clin. Nut., 1990, pp. 981-986, vol. 52.
Ainsworth, Barbara E., et al., "Compendium of Physical Activities: Classification of energy costs of human physical activities," Med. Sci. Sports Exerc., 1993, pp. 71-80, vol. 25, No. 1.
Leibel, Rudolph L., et al., "Changes in Energy Expenditure Resulting from Altered Body Weight," N.E.J.M., Mar. 5, 1995, pp. 621-628, vol. 332, No. 10.
Ainsworth, Barbara E., et al., "Compendium of Physical Activities: An update of activity codes and MET intensities," Med. Sci. Sports Exerc., 2000, pp. S498-S516, vol. 32, No. 9, Supp.
Watson, D., et al., "Effects of Continuous Vs. Fractionalized Exercise on Caloric Expenditure in Non-Obese Males and Females," Med. Sci. Sports Exerc., May 2002, p. S217, vol. 34. No. 5, Supp. 1.
Watson-Winfield, D., et al., "Continuous Vs. Fractionalized Exercise on Caloric Expenditure in Non-Obese and Obese Females," Med. Sci. Sports Exerc., May 2003, p. S106, vol. 35. No. 5, Supp. 1.
Jones. M.D., Val, "Resting Metabolic Rate: A Critical, Primary Care Screening Test," MedGenMed, Jun. 2006, p. 76, vol. 8, No. 2.
King, Neil A., et al., "Metabolic and Behavioral Compensatory Responses to Exercise Interventions: Barriers to Weight Loss," Obesity, 2007, pp. 1373-1383, vol. 15. No. 6.
Hansen, Dominique, et al., "The Effects of Exercise Training on Fat-Mass Loss in Obese Patients During Energy Intake Restriction," Sports Med., 2007, pp. 31-46, vol. 37, No. 1.
Rosenbaum, Michael, et al., "Energy intake in weight-reduced humans," Brain Res., 2010, pp. 95-102, vol. 1350.
Thomas, Tom R., et al., "Exercise and the metabolic syndrome with weight regain," J. Appl. Physiol., 2010, pp. 3-10, vol. 109.
Horie, Lilian M., et al., "New Specific Equation to Estimate Resting Energy Expenditure in Severely Obese Patients," Obesity, May 2011, pp. 1090-1094, vol. 19, No. 5.
International Search Report and Written Opinion for PCT Application No. PCT/US2012/049131, 12 pages.

* cited by examiner

CO$_2$ sensor – composite material on support

CO$_2$ and O$_2$ sensor response to 6L of exhaled breath

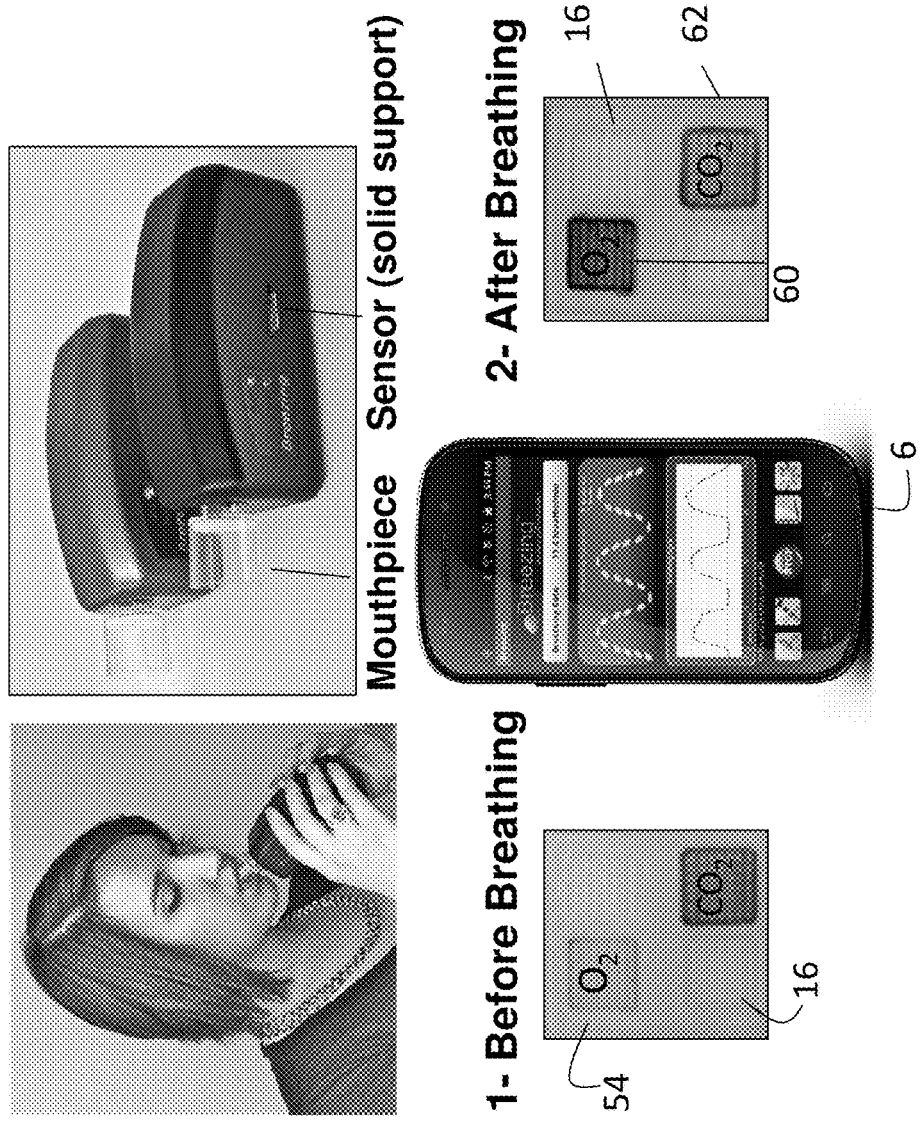

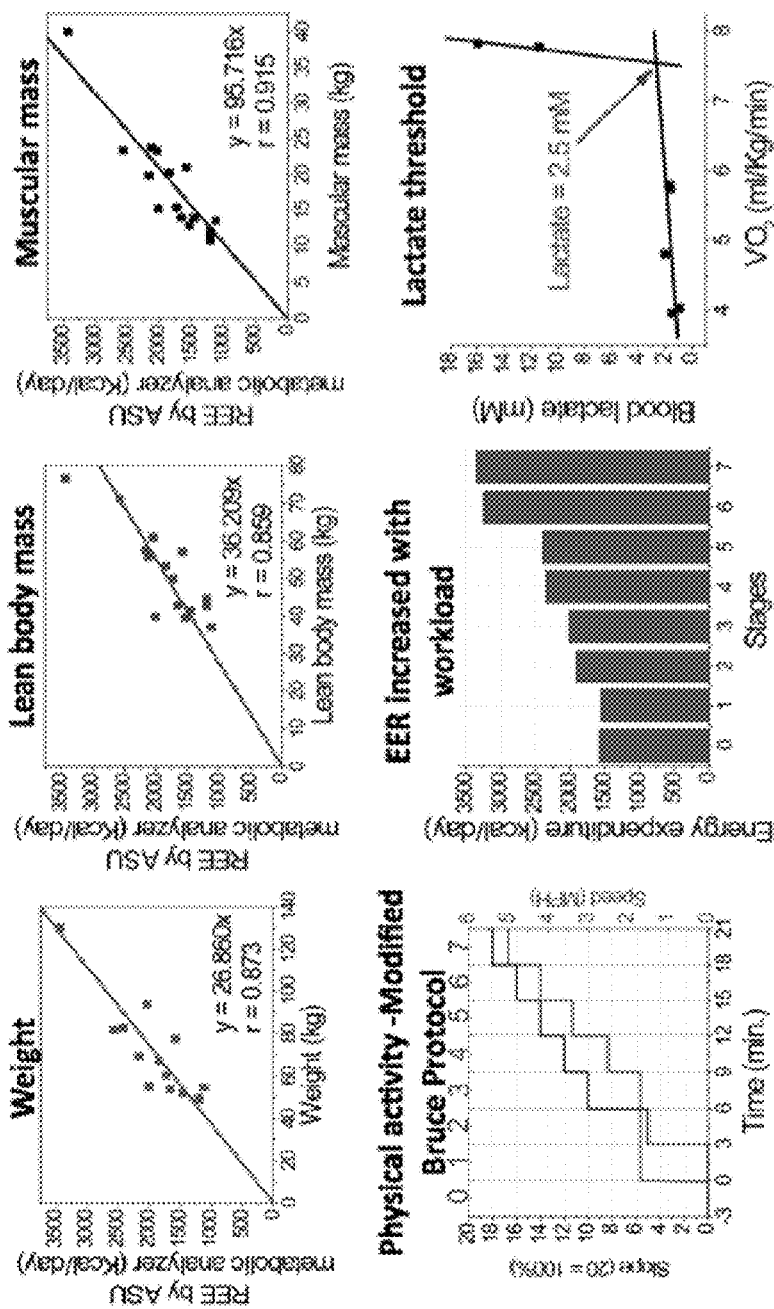

FIG. 11

| USING A METABOLIC ANALYZER TO MEASURES BOTH OXYGEN AND CARBON DIOXIDE |
| --- |
| 100 |

| MEASURING WEIGHT OF THE SUBJECT USING A WEIGHT MEASUREMENT DEVICE |
| --- |
| 102 |

| RECOMMENDING FOOD INTAKE AND/OR PHYSICAL ACTIVITY BASED ON AT LEAST THE READINGS OF THE METABOLIC ANALYZER AND WEIGHT OF THE SUBJECT |
| --- |
| 104 |

METABOLIC ANALYZER

CROSS-REFERENCE TO RELATED APPLICATIONS

The present application claims priority from U.S. provisional application No. 61/496,483, filed Jun. 13, 2011 and U.S. provisional application No. 61/514,194 filed Aug. 2, 2011, both entitled "METABOLIC ANALYZER." The contents of both referenced provisional applications are incorporated by reference.

TECHNICAL FIELD

The present invention relates to methods for performing indirect calorimetry, monitoring resting energy expenditure, fat burning rate and other physiological parameters. More particularly, the invention relates to methods for using metabolic analyzers that are based on detection of several metabolic signatures including detection of the rates of consumed oxygen and produced carbon dioxide, and concentrations of other metabolites in breath.

BACKGROUND

Existing technologies for indirect calorimetry and resting energy expenditure monitoring are typically based on electron paramagnetic resonance, electrochemical and infrared detection for detection of oxygen consumption rate and carbon dioxide production rate. The electron paramagnetic resonance method is humidity dependent, the electrochemical detection face challenging lifetime issues, and the infrared detection are prone to interference and fall short in selectivity and specificity. In addition, the cost of the analyzer combining these different detection principles in a single integrated device is expensive.[1] Even though a CPT insurance code has been established for using these technologies, the high cost inherent to these technologies prohibits them from reaching a larger consumer market.

Recently, other respiratory analyzers have been developed. One is for exercise use, which includes a single oxygen sensor and a wind guard.[2] Although this analyzer allows for assessment of oxygen consumption rate for sport activities, it does not detect carbon dioxide production rate, which is necessary for accurate detection of energy expenditure. It has been established that accurate assessment of energy expenditure and respiratory quotient requires one to detect both oxygen consumption and carbon dioxide production rates.[1] A wireless wearable mask including both oxygen and carbon dioxide sensors has been disclosed.[3] The sensors are two separated pieces, one detects oxygen, and the other one detects carbon dioxide, and the two pieces are based on different sensing principles. While the oxygen sensor is based on galvanic fuel cell detection, the carbon dioxide sensor is based on infrared detection using a concave-wall and reflective-surface. Although the analyzer can detect both oxygen and carbon dioxide, the use of different detection principles and separated pieces adds complexity to the system, making it expensive and bulky. Furthermore, the galvanic fuel cell for oxygen detection faces the limitation of electrochemical techniques mentioned above.

One publication describes simultaneous detection of oxygen and carbon dioxide using a single detection principle.[4] The system is based on the detection of fluorescence light emitted from fluorophore molecules upon excitation, typically UV or high-energy light. It has been applied to monitor carbon dioxide and oxygen for micro-organism cultures, but not for analysis of metabolites in breath. Fluorophores are prone to humidity and temperature changes, so the approach may not be suitable for detection of oxygen and carbon dioxide in breath. In addition, the fluorescence detection faces photo-bleaching issue, requires low noise and sensitive photodetector, and UV light source, which make it undesirable for a low cost and miniaturized device.

Acetone is another metabolite that is indicative of fat burning. Several devices have been disclosed related to measuring acetone. Some of them are based on electrochemical[5-7] and electrical[8-10] measurements.

One example of electrochemical detection uses enzymes.[5-7] Such devices face stability challenges and require controlled humidity conditions.[11] Examples of existing electrical sensors are based on metal-oxide devices,[8-9] or nanoparticle devices.[10] Unfortunately the metal-oxide devices require high temperatures during operation, leading to high power consumption. Similar difficulties are presented by the nanoparticle devices in that they require pattern recognition algorithms which are difficult to implement in complex changing sample matrixes such as when monitoring breathing.

Another acetone apparatus has been disclosed for metabolic fitness training.[12] The device provides only a qualitative measure of acetone levels of maximum fat burn rate. An additional limitation of the device is that it does not detect oxygen and carbon dioxide, which are needed for energy expenditure and respiratory quotient assessment. Yet another acetone apparatus for diabetic diagnosis has been disclosed.[13] The apparatus employs a microplasma source in combination with a spectrometer. The microplasma approach requires bulky instrumentation, high power to produce excited acetone fragments from the breath gas, and it is difficult to miniaturize.

The metabolic analyzer disclosed here for the first time overcomes sensitivity, selectivity, stability, cost and power consumption problems found in known devices and systems. In contrast to known devices and systems, the instant disclosure describes a new and novel metabolic analyzer based on the detection of several metabolic signatures via distinct color changes of sensing materials coated onto a solid support. Each sensing material is designed such that they interact and react specifically with each metabolic analytes, including oxygen, carbon dioxide, acetone and other metabolites. These sensing materials can be deposited on the same support to create an array such that each sensor in the array detects specifically one metabolite. In comparison to fluorescence detection schemes that measure weak emission of light,[4] the color detection apparatus in the present disclosure measures absorption of light, which requires neither low noise and sensitive photodetectors, nor UV light sources.

A basic configuration of the metabolic analyzer detects at least both oxygen and carbon dioxide, which allows for indirect calorimetry that evaluates a person's energy expenditures (kcal/day) from the rates of consumed oxygen and produced carbon dioxide in breath. The analyzer also provides respiratory quotient (RQ) from the ratio of oxygen to carbon dioxide, which indicates the type of food substrate metabolized, and or the breathing status under an aerobic or anaerobic exercise condition. Such a capability will benefit the large and growing obese and overweight population, and also provide more effective training of athletes and armed forces. Unlike physical activity monitoring devices, such as accelerometers, which cannot monitor resting energy expenditures, the instant invention's indirect calorimeter specifically targets resting energy expenditure. This is important because over 75% of a person's energy expenditure is resting energy.[14]

In another advance over existing techniques and devices also disclosed here for the first time is a ketone (for example, acetone) detection capability built into the metabolic analyzer. Acetone level measurements provide extra information about metabolism and can discriminate fat vs. carbohydrates burning. The energy expenditure, together with acetone detection capability, provides additional values for more effective weight loss and control, and physical training programs.

In brief, the novel metabolic analyzer disclosed hereinbelow can measure Energy Expenditure (EE) and Respiratory Quotient (RQ). The EE quantifies the amount of calories consumed by the body either at resting state (Resting Energy Expenditure, REE), or during an activity (office work, work bench, computer work, etc). The RQ determines the type of dominant food substrate metabolized by the body. Both parameters are calculated from the measurement of consumed oxygen rate and produced carbon dioxide rate. The novel metabolic analyzer disclosed here for the first time enables more effective weight management and fitness applications as described below.

Various methods for weight and fitness management have been developed and practiced. Some methods include use physical sensors, such as accelerometers, to evaluate the energy expenditure of a person during exercise. However, exercise activities represent only a small percentage (<15%) of the person's energy expenditure averaged in a day[15] Other approaches consider more accurate strategies, including actual exercise, and calories intake to forecast weight changes.[16,17] Although these approaches are more accurate, they still lack of the determination of the major component of energy expenditure on a day, the resting energy expenditure, which not only enables more accurate determination of total energy expenditure (TEE), but also more importantly an indication of the metabolic stage of the person's body during a weight loss or fitness plan.

In order to overcome the problem, methods including metabolic rate measurement (e.g. resting energy expenditure) have been proposed. One method involves measuring metabolic rate and body composition using a plethysmographic air chamber, magnetic resonance imaging or computed tomography.[18] The method also includes consultation of a nutritional counselor. The counselor evaluates the metabolic rate and body composition, provides advice for weight management and determines the weight goal accomplishments. In addition, the method includes a massage therapy reward if the person reaches the goal. Although the method is complete, and accurate, the use of bulky instrumentation for assessment of body composition precludes the implementation of the method at the person's home, office or ordinary living physical places.

In a separate approach, the use of a portable indirect calorimeter is proposed to obtain resting metabolic rate, and data of food intake and activities are used as a method of health management plan.[19] Although the method includes free-living conditions measures, the use of data of food intake makes the method cumbersome. It is has been well established that it is difficult keep accurate tracking of food intake, and these methods lead to problems of under-reporting.

More recent publications have recognized the problem of food intake data, and proposed alternative approaches. One such approach is a method comprising energy expenditure, and modeling.[20] The model is used to predict a weight value at a predetermined period of time. The prediction can be made based on energy expenditure and an initial weight measure. Although the method is accurate, it focuses on prediction of weight at a fixed period of time, and precludes any additional outcome or recommendation at non-fixed time periods, or new weight values (which could include target weights). Another system proposes the assessment of unambiguous food energy intake via the assessment of metabolic rate and body composition change.[21] Although the system may be accurate, it requires measuring at least two parameters, body composition, and energy expenditure, each of which currently requires dedicated devices. On the other hand the assessment of body composition is complex, and still needs development of more accurate portable measurement devices.

Instead of focusing on measuring parameters that are either inaccurate or difficult to track (like food intake) or misrepresentative (like physical activity), the present invention focuses on key parameters that are meaningful yet easily and accurately measurable. These parameters include weight, REE and RQ of a person. Weight can be readily measured with various commercial devices, and REE and RQ can be measured with the metabolic analyzer disclosed in our prior application. Recommendations on diet and physical exercises are made based on the values and changes of the weight, REE and RQ, and the person's weight and fitness goal. The method may also include sensors that track physical activity-energy expenditure to provide total energy expenditure information, and imaging or video processing of the person's progress of a weight and fitness program.

BRIEF SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a method for weight and/or fitness management using a metabolic analyzer that measures metabolic data including oxygen and carbon dioxide is disclosed. The metabolic analyzer includes a plurality of integrated collection-detection sensors with for high efficiency and collection, high specificity and simultaneous detection of at least two metabolic signatures, including at least oxygen and carbon dioxide, in breath via a solid support with high density of sensing binding sites, where the solid support includes sensing materials such that the sensing binding sites are specific to the metabolic signatures, and change colors upon interactions with the metabolic signatures. Weight of the subject is measured using a weight measurement device and a recommendation for food intake and/or physical activity is based on at least the readings of the metabolic analyzer and weight of the subject.

In another aspect, measuring metabolic data includes measuring initial resting energy expenditure (REE) and total energy expenditure (TEE).

Another aspect, includes operating the metabolic analyzer to recommend an initial calorie intake where, if the subject has a normal body mass index (BMI), the recommended calorie intake is equal to TEE, if the subject has overweight or obese BMI, the recommended calorie intake follows published guidelines and also recommends how many minutes of a given activity the subject will need to meet the calories reduction target. After a first recommendation, follow-up recommendations are based on the changes of REE, TEE, and weight (WT).

In another aspect, the at least two metabolic signatures further include ketones, including acetone, sulfur compounds, including hydrogen sulfide, ammonia and water.

In another aspect, the method of further includes introducing breath through a mouthpiece monitoring breath volume or rate from the mouthpiece illuminating at least one light sensor; and detecting changing colors of the plurality of integrated sensors that include a porous membrane coated with sensing materials, which change color upon interactions with target analytes.

In another aspect, the at least one light sensor includes a photodetector, complementary metal oxide semiconductor (CMOS) or a charge-coupled device (CCD) for detecting color changes from which the analyte concentrations are determined.

In another aspect, monitoring breath volume or rate comprises operating a flow meter or a pressure sensor from which the breath volume or rate is determined.

In another aspect, monitoring breath volume or rate comprises coupling a bag with a fixed volume to collect a breath after passing it through the membrane in a timed period.

In another aspect the method includes generating a signal with the light sensor and transmitting the signal to a mobile device, where the relevant data are processed, displayed, stored and further transmitted.

In another aspect, the method includes locating the plurality of integrated sensors on the mouthpiece so that breath passes through the solid support to facilitate reactions of the analytes in the breath with the sensing materials coated on the membrane.

In another aspect, the method includes locating the plurality of integrated sensors on the mouthpiece so that breath passes over the solid support to facilitate reactions of the analytes in the breath with the sensing materials coated on the membrane.

In another aspect, the method includes locating the light source and the light sensor at the opposite sides of the sensor so that light from the light source transmitted through the sensor is detected by the light sensor.

In another aspect, the method includes locating the light source and light sensor on the same side relative to the solid support such that the reflected or scattered light from the membrane is detected.

In another aspect, the method includes an electronic circuit that controls and wirelessly transmits the signals to an external device.

In another aspect, the method includes integrating at least the mouthpiece, the light source, and the sensors into a unitary device.

In another aspect, the porous membrane includes sensing materials in the shape of nanoparticles or microparticles having high density binding sites.

In another aspect, the solid support comprises a material selected from the group consisting of synthetic polymers, natural polymers, polyester, nylon, cellulose, glass-based substrates, fiber glass, sol gel, silica, alumina, silica gel and composites thereof.

In another aspect, the method further includes monitoring metabolic processes including integrating a sensor in a cell phone; and using the sensor for detecting consumed oxygen rate and produced carbon dioxide rate from breath obtained with a fixed volume in a timed period.

In another aspect, the method further includes integrating the sensor in a cell phone; and using the sensor for detecting consumed oxygen rate and produced carbon dioxide rate from breath expiratory rates obtained from a pressure sensor or flowmeter.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 2A' and FIG. 2B' show a schematic representation of a sensor coated with composite sensing materials, where the sensor has compartments with different sensing and reference areas enabling detection of breath analytes via color changes.

FIG. 3A' and FIG. 3B' illustrate the use of and results from sensing materials of a solid support sensor.

FIG. 6' schematically shows a process for using a metabolic analyzer in combination with a cell phone.

FIG. 8A-8A2 show a cross-sectional study performed with the metabolic analyzer including REE trends with physical parameters of (A) weight, (A1) lean body mass, and (A2) muscular mass.

FIGS. 8B-8B2 show energy expenditure change with physical activity including (B) increased load in a treadmill, (B1) corresponding REE and EE rate curve and (B2) lactate curve, indicating lactate threshold, determined by $VO_2$ measures. The value of blood lactate threshold (2.5 mM)

matches the literature values, and indicates the capability of $VO_2$ to determine anaerobic metabolic conditions, under physical activities.

Figure 9B:
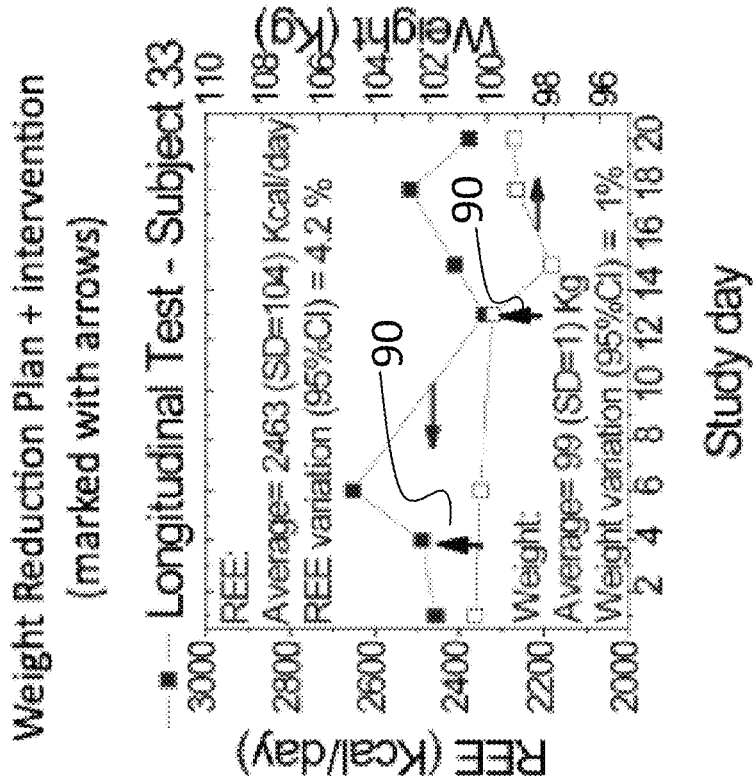
Figure 9A:
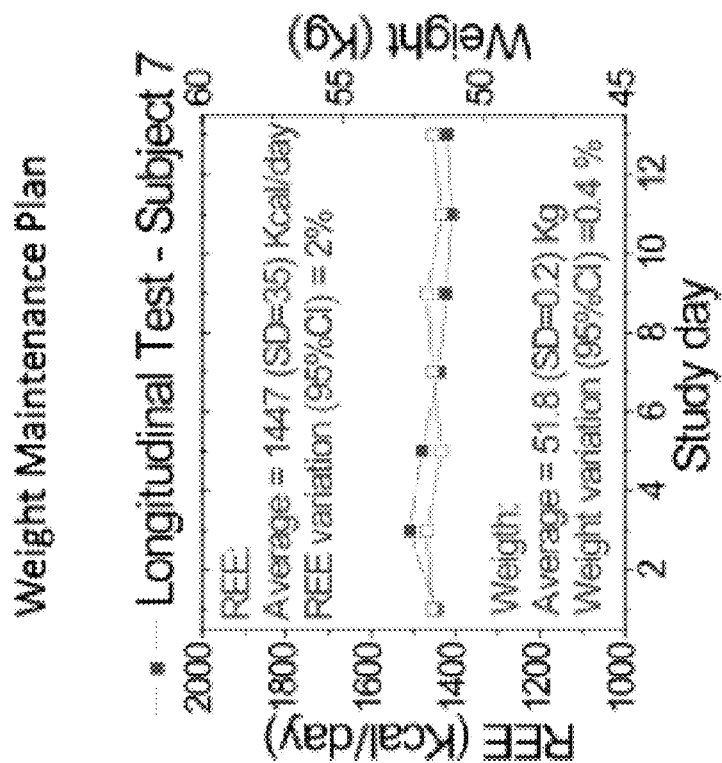

FIGS. 9A and 9B respectively show REE and weight profiles of subject underweight maintenance plan (left), and weight reduction intervention plan.

Figure 10:
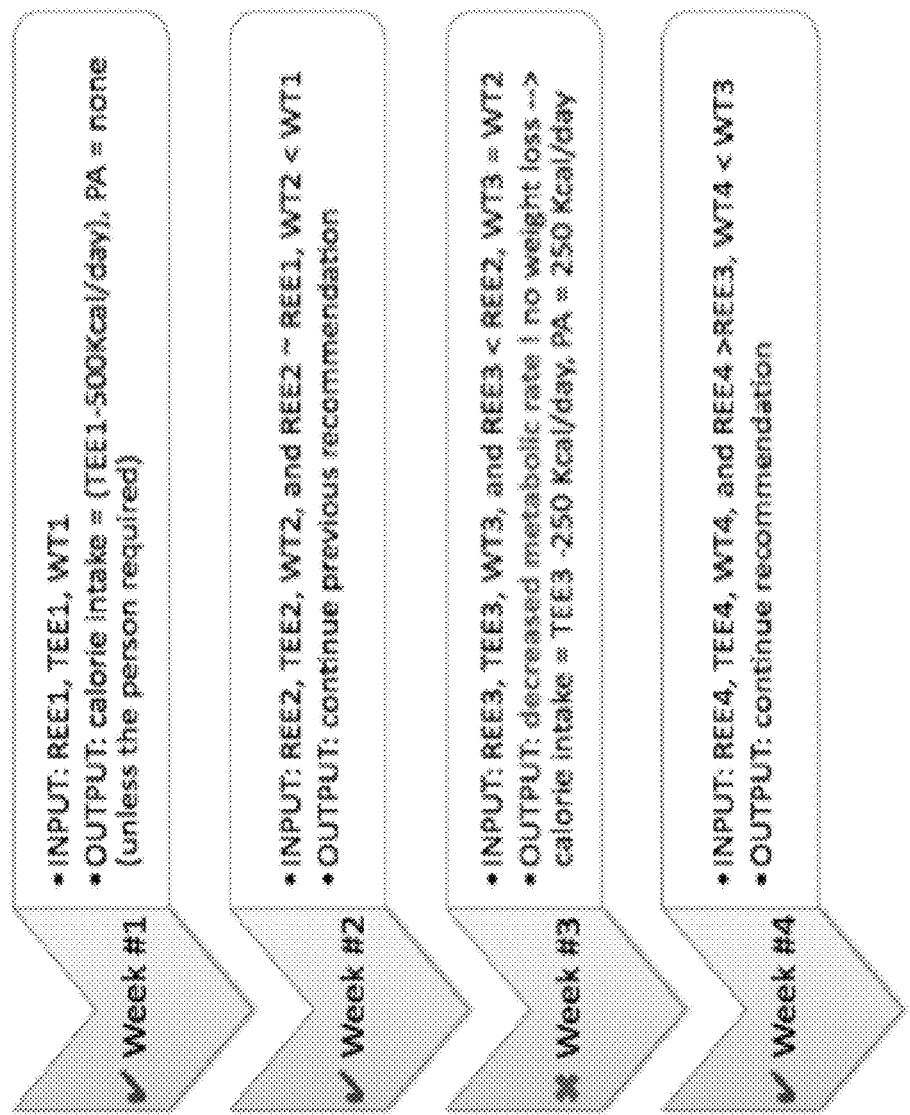

FIG. 10 shows an expected scenario from weight (WT) management in obese or overweight subjects.

FIG. 11 schematically shows a high level flow chart of an example of a method for weight and/or fitness management.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments for metabolic analyzers that are based on detection of several metabolic signatures. Several features of methods and systems in accordance with example embodiments are set forth and described in the Figures. It will be appreciated that methods and systems in accordance with other example embodiments can include additional procedures or features different than those shown in the Figures. Example embodiments are described herein with respect to analysis of environmental conditions. However, it will be understood that these examples are for the purpose of illustrating the principles, and that the invention is not so limited. Additionally, methods and systems in accordance with several example embodiments may not include all of the features shown in the Figures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of sample collection or analysis:

As used herein, "plurality" is understood to mean more than one. For example, a plurality refers to at least 3, 4, 5, 70, or more.

As used herein, "cellular telephone" (or "cell phone") has its generally accepted meaning and includes any portable device that can make and receive telephone calls to and from a public telephone network, which includes other mobiles and fixed-line phones across the world. It also includes mobile devices that support a wide variety of other services such as text messaging, software applications, MMS, e-mail, Internet access, short-range wireless communications (for example, infrared and Bluetooth).

As used herein, "tablet computer" has its generally accepted meaning and includes any mobile computer including a complete mobile computer, larger than a mobile phone or personal digital assistant, integrated into a flat touch screen and primarily operated by touching the screen such as, for example, an Apple Ipad® tablet computer.

Example Embodiments

Figure 1A:
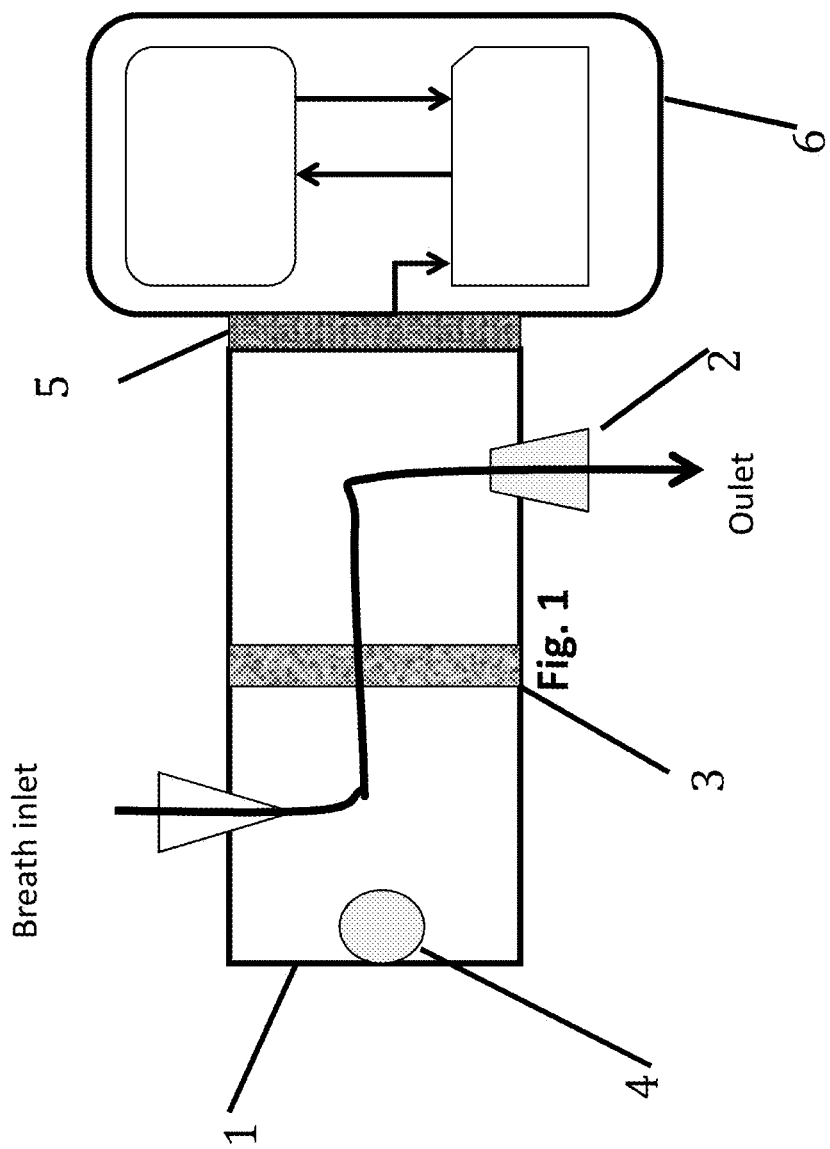
FIG. 1A schematically shows an example of a metabolic analyzer in which breath sample flows through a porous solid support coated with sensing materials.

Referring now to FIG. 1A, an example of a metabolic analyzer is schematically shown. It contains several components: 1) an integrated collection-detection sensor with high efficiency for collection and detection of metabolic signatures via a porous membrane with high density of sensing binding sites, which provides optimal sensitivity, 2) integration of the collection-detection sensors (porous membrane sensor) with solid-state optical detection, which features low cost and robust device, 3) sensing materials with specific and reactive binding sites that not only support high sensitivity but also high specificity for correct detection of breath analytes.

Figure 1B:
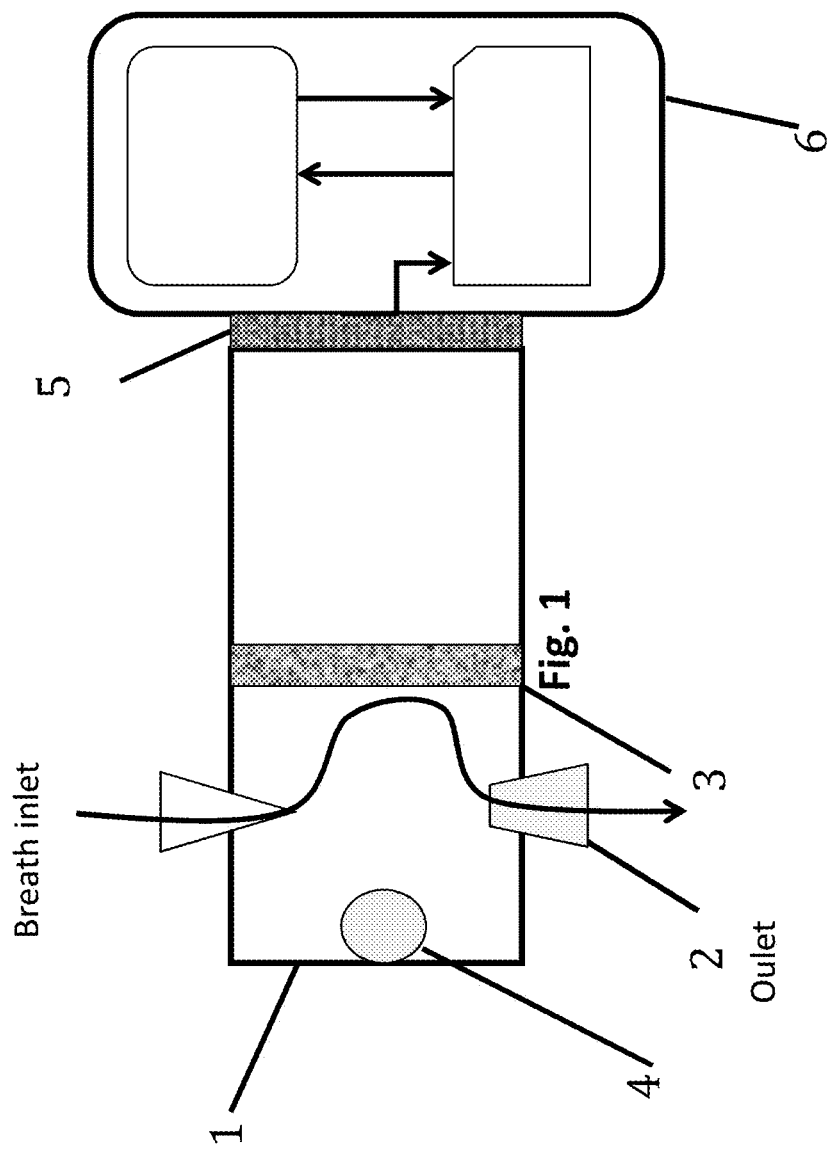
FIG. 1B schematically shows an example of a metabolic analyzer in which breath sample flows over a solid support coated with sensing materials.

Referring now to FIG. 1B, another example of a metabolic analyzer is schematically shown. It contains several components: 1) an integrated collection-detection sensor with high efficiency for collection and detection of metabolic signatures via a solid support coated with a high density of sensing binding sites, which provides optimal sensitivity, 2) integration of the collection-detection sensors (porous membrane sensor) with solid-state optical detection, which features low cost and robust device, 3) sensing materials with specific and reactive binding sites that not only support high sensitivity but also high specificity for correct detection of breath analytes.

The metabolic analyzers as described in FIGS. 1A and 1B can perform simultaneous detection of breath analytes, including carbon dioxide, oxygen, and acetone. It has a mouthpiece 1 that can be paired with a mobile device 6, such as cellular phone or tablet computer. The mouthpiece 1 consists of an inlet for the user to introduce breath in it, a means to monitor breath volume or rate 2, a light source 4, a sensor 3 and supporting components. The sensor 3 is a porous membrane (FIG. 1A) such that the user can blow his/her breath through it comfortably without assistance of additional mechanical components, such as pumps. Alternatively, as shown in FIG. 1B, the sensor 3 is solid support and the user blows his/her breath over the surface of the sensor. The sensor is coated with sensing materials, which change color upon interactions with the target analytes ($O_2$, $CO_2$ and acetone). The light source 4 illuminates the membrane and a light detector 5 detects the color changes from which the analyte concentrations are determined. The signal is transmitted to the mobile device 6, where the relevant data are processed, displayed, stored and transmitted to a designated device.

Figure 6:
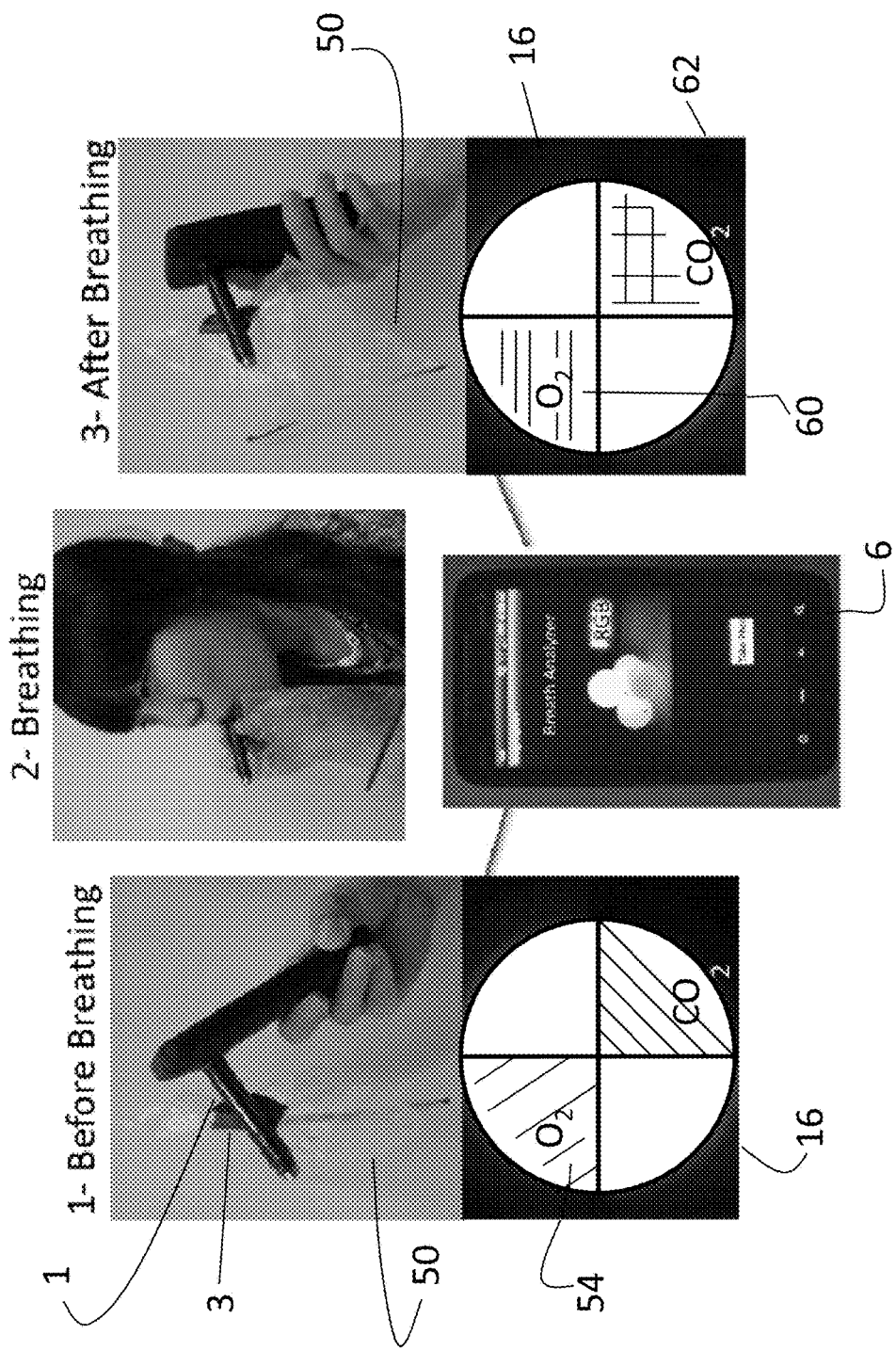
FIG. 6 schematically shows a process for using a metabolic analyzer incorporated into a cell phone.
Figures 7A, 7B, 7C, 7D:
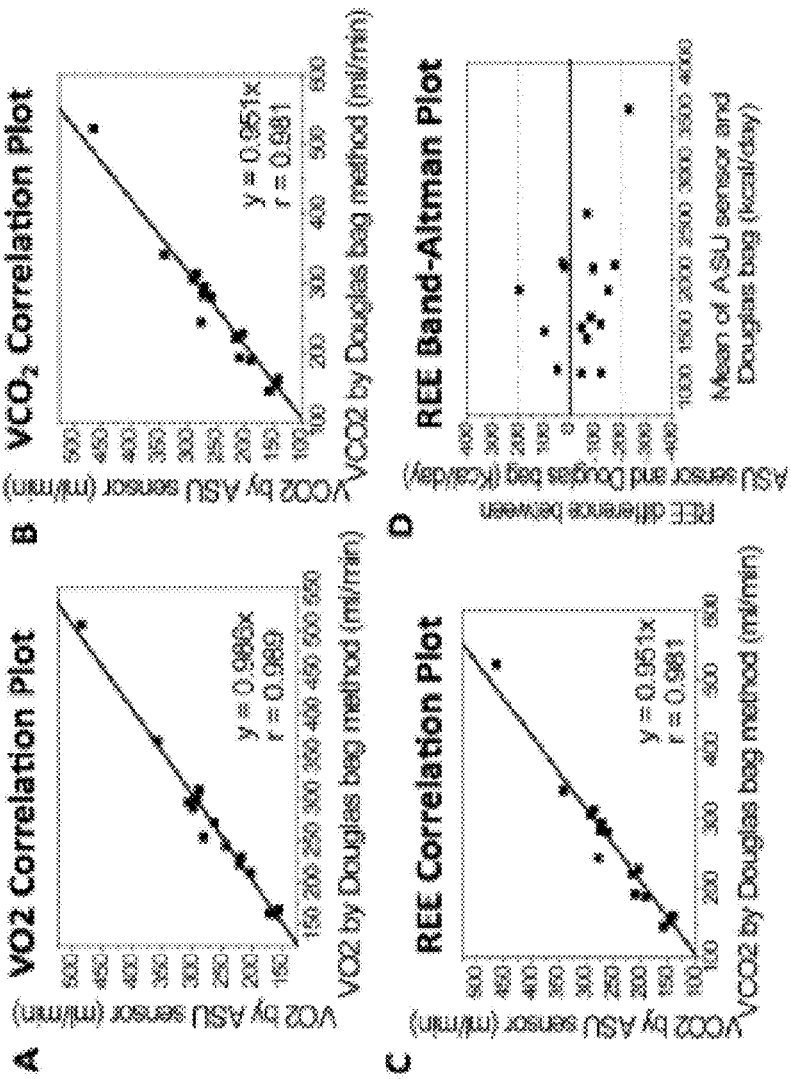
FIGS. 7A-D show correlation results of: (A) oxygen consumption rate (VO2), (B) carbon dioxide production rate (VCO2), and REE (C) from ASU metabolic analyzer vs. Douglas bag method. (D) Bland-Altman plot for REE measures performed with ASU metabolic analyzer vs. Douglas Bag Method.

The mouthpiece 1 includes at least an inlet 10 to allow a user to blow his/her breath into it. A means to monitor breath volume or rate 2 may advantageously include a flow meter or a pressure sensor from which the breath volume or rate is determined. An alternative means may include a bag (as shown in FIG. 6) with a fixed volume to collect the breath after passing it through the membrane or over the solid support in a timed period.

Figures 2A, 2B:
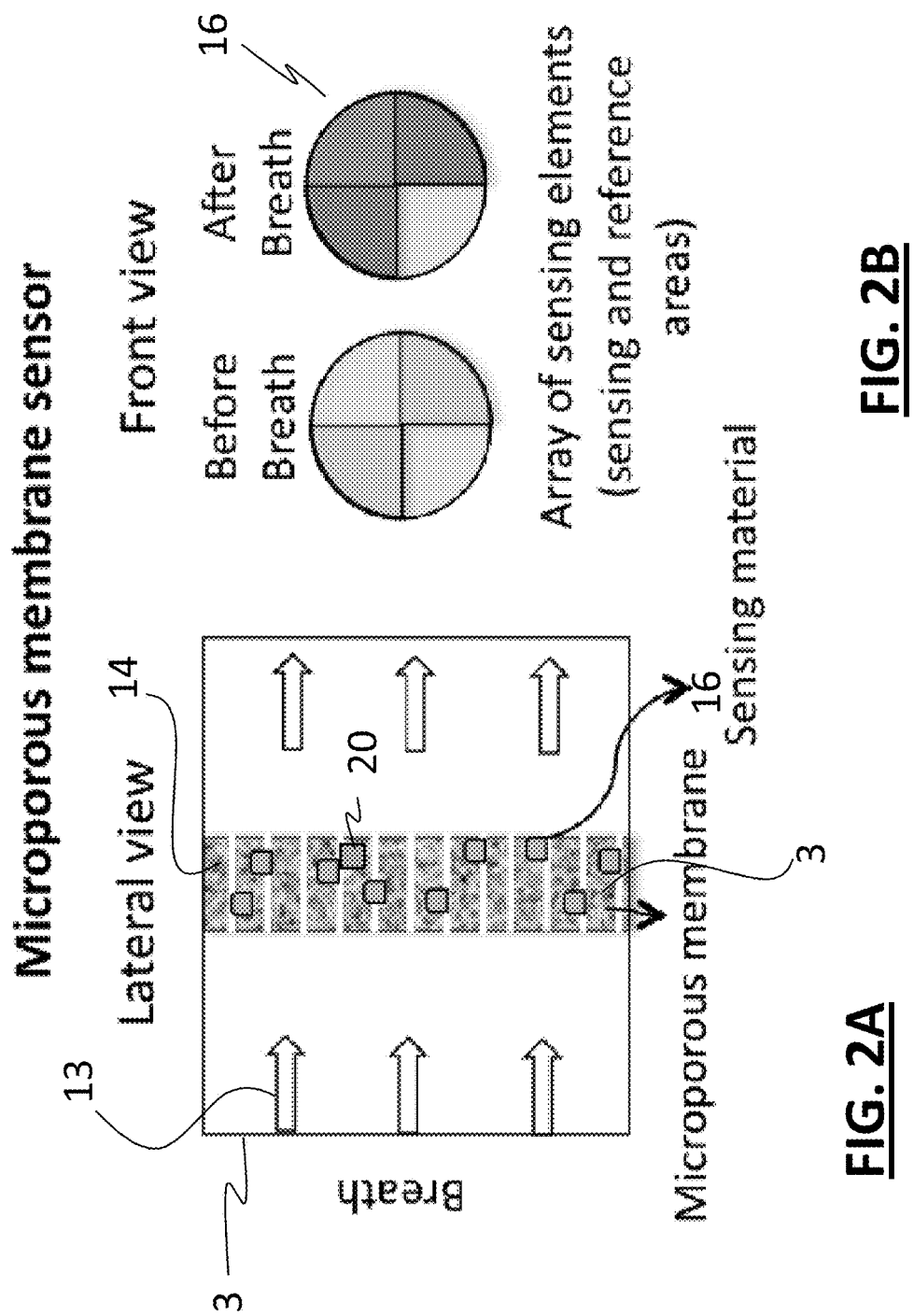
FIG. 2A and FIG. 2B show a schematic representation of a sensor embedded with composite sensing materials, where the sensor has compartments with different sensing and reference areas enabling detection of breath analytes via color changes.

Referring now jointly to FIG. 2A and FIG. 2B, a schematic representation of a porous membrane sensor embedded with composite sensing materials is shown, where the membrane has compartments with different sensing and reference areas enabling detection of breath analytes via color changes. In one example embodiment, the sensor 3 comprises a porous membrane 14 on which an array of sensing materials 16 is printed. Breath flow is indicated by the directional arrows 13. As breath containing analytes flows into the sensor 3, the array of sensing materials 16 react with the analytes and lead to color changes. The membrane 14 has also at least one area 20 designated as a reference area to correct drifts, remove noise and facilitate accurate detection of the color changes. The reference area 20 is either a blank membrane area or coated with materials that are insensitive to the analytes. The size and density of the membrane pores are selected to allow breath to pass the membrane with different and desirable flow rates. In some useful embodiments, the membrane 14 includes either a pure or composite material, including synthetic and natural polymers (e.g. polyester, nylon, cellulose), glass-based or like substrates (e.g. fiber glass, sol gel), and particles (e.g., silica, alumina and silica gel).

The membrane 14 is preferably selected to allow light to partially transmit through it. It can be assembled as part of a disposable sensor cartridge, which can be used for on-line or off-line breath analysis. In the case of on-line analysis, the sensor can be integrated together with the mouthpiece, and the pore size of the sensor porous membrane controlled to allow either free or controlled flow conditions. In the case of off-line analysis, the sensor can be inserted in a sensing chamber, which provides appropriate sample delivery from a pre-collected breath sample via a forced flow system.

Referring now jointly to FIG. 2A' and FIG. 2B', a schematic representation of a solid support coated with composite sensing materials is shown, where the solid support has compartments with different sensing and reference areas enabling detection of breath analytes via color changes. In one example embodiment, the sensor 3 comprises a solid support 14 on which an array of sensing materials 16 is printed. Breath flow is indicated by the directional arrows 13. As breath containing analytes flows into the sensor 3, the array of sensing materials 16 react with the analytes and lead to color changes. The solid support 14 has also at least one area 20 designated as a reference area to correct drifts, remove noise and facilitate accurate detection of the color changes. The reference area 20 is either a blank area or coated with materials that are insensitive to the analytes. The size and density of the membrane pores are selected to allow breath to pass over the solid support with different and desirable flow rates. In some useful embodiments, the solid support 14 includes either a pure or composite material, including synthetic and natural polymers (e.g. polyester, nylon, cellulose), glass-based or like substrates (e.g. fiber glass, sol gel), and particles (e.g., silica, alumina and silica gel).

The light source is preferably a white LED to provide illumination of the sensor at different wavelengths simultaneously. The LED built in the mobile device may also be used. In some cases, white light may be obtained from ambient light. In other cases, a combination of other color LED or a combination of different LEDs, may be used. The light sensor can be discrete photodetectors, arrays of photodetectors, a CCD or a CMOS imager. A preferable configuration is to use the built-in camera in the mobile device to minimize the need of a detection circuit and signal transmission and lower the cost. The user interface uses preferably a mobile device, such as cell phone.

In one example embodiment, the mouthpiece 1, the light source 4, the sensor 3 and the photodetector components are integrated into single piece. The sensor is placed on the mouthpiece so that breath is in contact with the sensor to facilitate fast and efficient reactions of the analytes in the breath with the sensing materials. The light source and light sensor are placed at the opposite sides of the sensor so that light from the light source transmitted through the sensor is detected by the light sensor.

In an alternative arrangement the light source and light sensor are placed on the same side relative to the sensor such that the reflected or scattered light from the sensor is detected. An electronic circuit controls the LED, and conditions the output signals of the light sensor, and transmits the signals wirelessly to an external device. The external device further processes the signals, display and store and transmit data to other devices.

Alternatively, the light sensor is the CMOS or CCD in a mobile device, such as cell phone, tablet computer, pad, laptop, personal computer, or wristwatch. In this case, the mouthpiece containing components 2-4 is attached to the mobile device also provides signal processing and data storage, display and transmission.

In a useful embodiment, the sensor may advantageously contain sensing elements that determine $O_2$ and $CO_2$ for energy expenditure monitoring. Alternatively, the sensor contains sensing elements that determine acetone for fat burning monitoring. In yet another alternative embodiment the sensor may contain sensing elements for $O_2$, $CO_2$ and acetone detections such that both energy expenditure and fat burning rates are monitored. Alternatively, the sensor can contain sensing elements that determine $O_2$, $CO_2$, and/or acetone and/or ammonia, and/or hydrogen sulfide.

Device Examples

The sensor is a key component of the metabolic analyzer, not only because of its formulation but also because of its morphology, and intimate contact with the breath sample. We have tested the sensor for detection of carbon dioxide and oxygen in breath.

Carbon Dioxide Detection with Porous Membrane Sensor

Figure 3A:
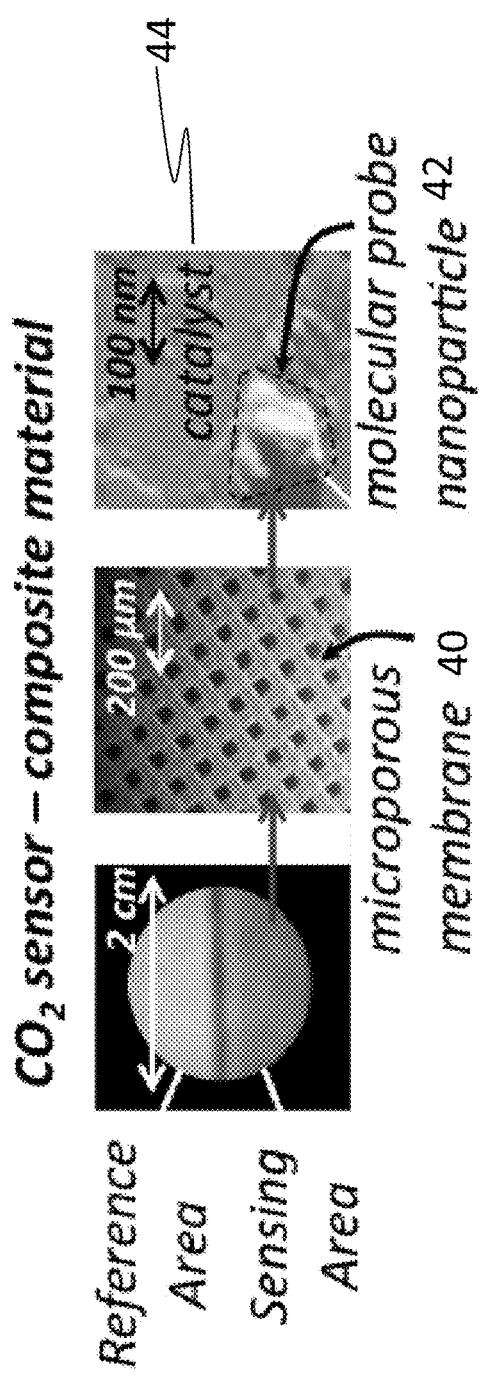
FIG. 3A and FIG. 3B illustrate the use of and results from sensing materials of a porous membrane sensor.
Figure 3B:
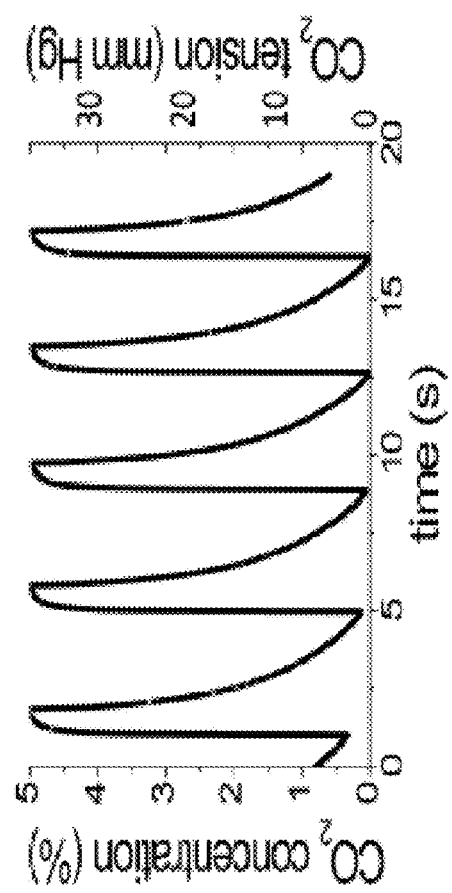
Figure 3A:
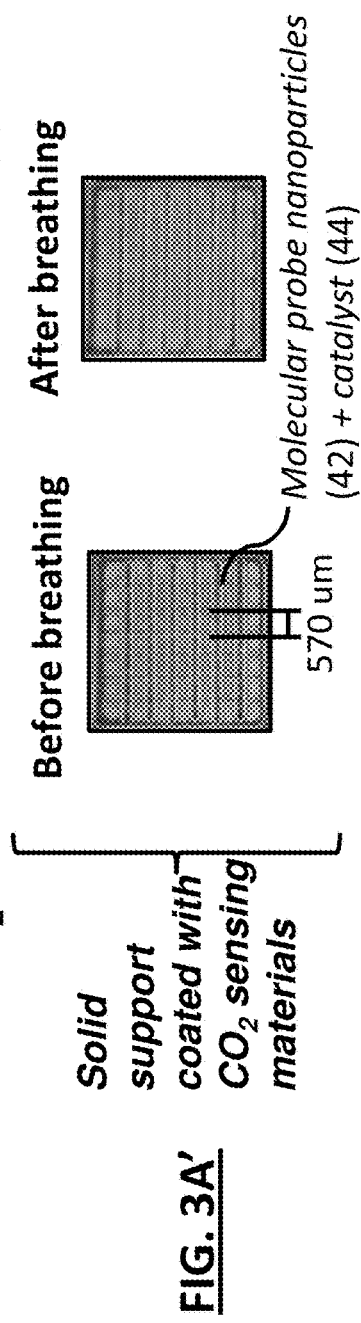
Figure 3B:
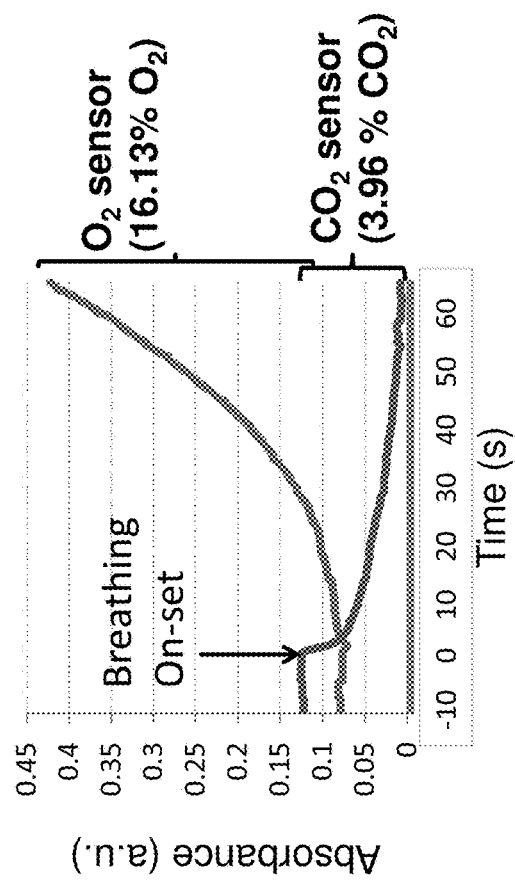

Referring now jointly to FIG. 3A and FIG. 3B, there shown are schematics of sensing materials of a porous membrane sensor. Referring specifically to FIG. 3A, pictures (left to right) of a $CO_2$ sensor, and sensing material: microphotography of a microporous membrane 40, and Atomic Force Microscope image of the composite sensing material formed by molecular probe nanoparticles 42 and a catalyst 44. The sensing material in the shape of nanoparticles, shows high reactivity and reaction kinetics for colorimetric gas sensing of carbon dioxide.

Referring specifically to FIG. 3B, $CO_2$ monitoring using the composite sensing material from $CO_2$ sensor, and sensing material is plotted. $CO_2$ concentration (%) is measured on the left vertical axis, with $CO_2$ tension (mmHg) measured on the right vertical axis, both plotted against time (s) on the horizontal axis.

Carbon Dioxide and Oxygen Detection with Solid Support Sensor

Referring now jointly to FIG. 3A' and FIG. 3B', there shown are schematics of sensing materials of a solid support sensor. Referring specifically to FIG. 3A', pictures (left to right) of a $CO_2$ sensor, and sensing material: microphotography of a solid support surface 40 with composite sensing material formed by coating the surface with molecular probe nanoparticles 42 and a catalyst 44. The sensing material in the shape of nanoparticles, shows high reactivity and reaction kinetics for colorimetric gas sensing of carbon dioxide.

Referring specifically to FIG. 3B', $CO_2$ and $O_2$ monitoring using the composite sensing material from $CO_2$ and $O_2$ sensing areas are plotted. Optical absorbance, corresponding to $CO_2$ and $O_2$ concentrations (%), are measured on the left vertical axis, plotted against time (s) on the horizontal axis.

Figure 4A:
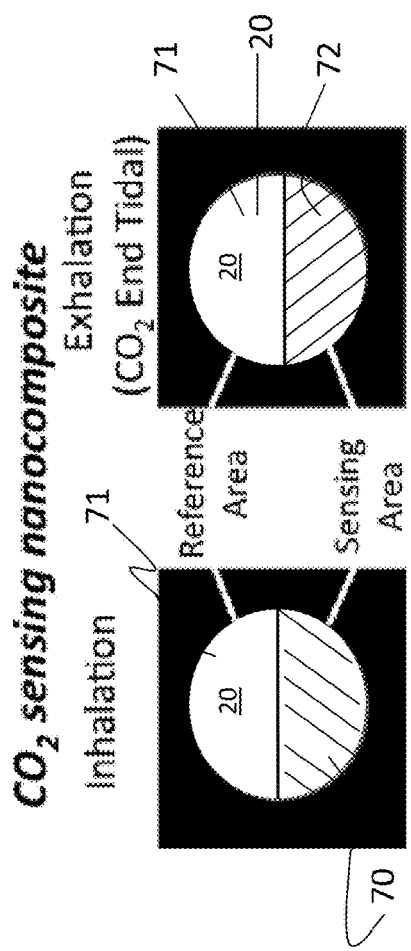
FIG. 4A schematically shows an example of detection of carbon dioxide from sensing color properties in a microporous membrane sensor.
Figure 4B:
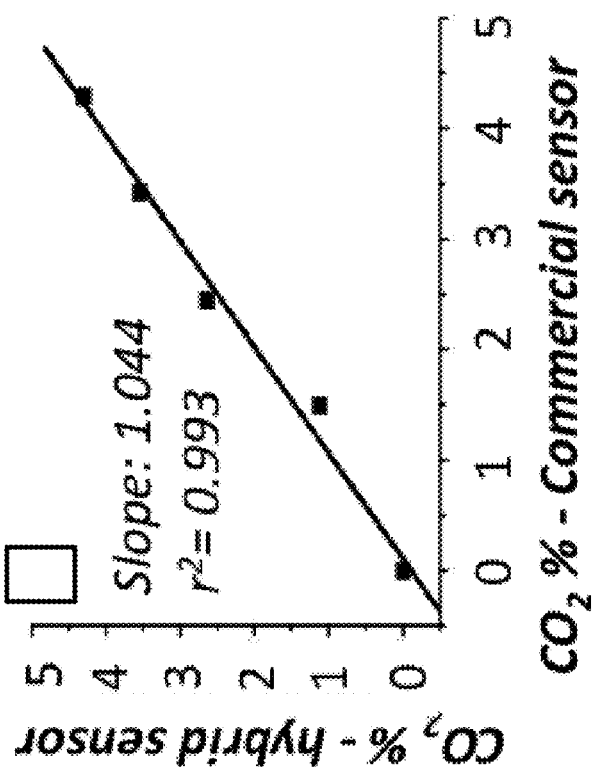
FIG. 4B illustrates accuracy for detection of carbon dioxide in artificial (1.5 & 2%) and real (3.5 & 4.3%) breath samples: correlation of the microporous membrane sensor with a commercial sensor based on infrared detection.

FIG. 4A schematically shows an example of detection of carbon dioxide with a microporous membrane sensor sensing material color properties. In the case of carbon dioxide, the composite sensing material has the following components with respective specific functions. As illustrated by lower sensing areas 70 and 72 respectively, the molecular probe is a pH sensitive dye that turns from blue into yellow upon contact with $CO_2$ via generation of bicarbonate ions ($HCO_3^-$) and protons ($H^+$) in the humid breath environment of inhalation and exhalation. Another component of the composite is a hydroxide, which acts as a catalyst between the molecular probe (solid phase) and $CO_2$ (gas phase). As described above, the sensing materials are cast on a porous membrane with pre-defined sensing (70 and 72) and reference areas (71). The integration of the membrane sensor to a device with an integrated LED, which can be attached to a cell phone camera has been performed. The integrated device has demonstrated usefulness for detection of carbon dioxide in artificial and real breath samples as shown in FIG. 4B.

Oxygen Detection with Porous Membrane Sensor

Figure 5B:
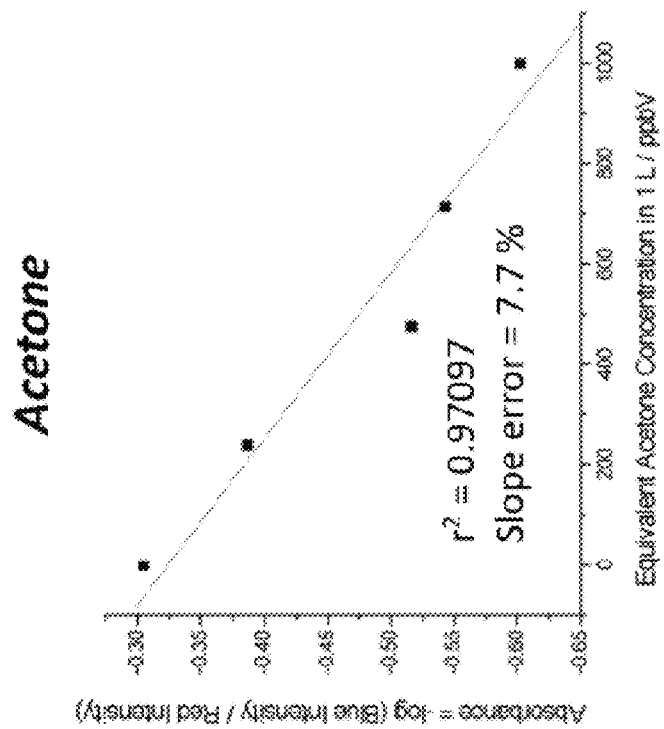
FIG. 5B graphically shows an example of detection of acetone with membrane sensor.
Figure 5A:
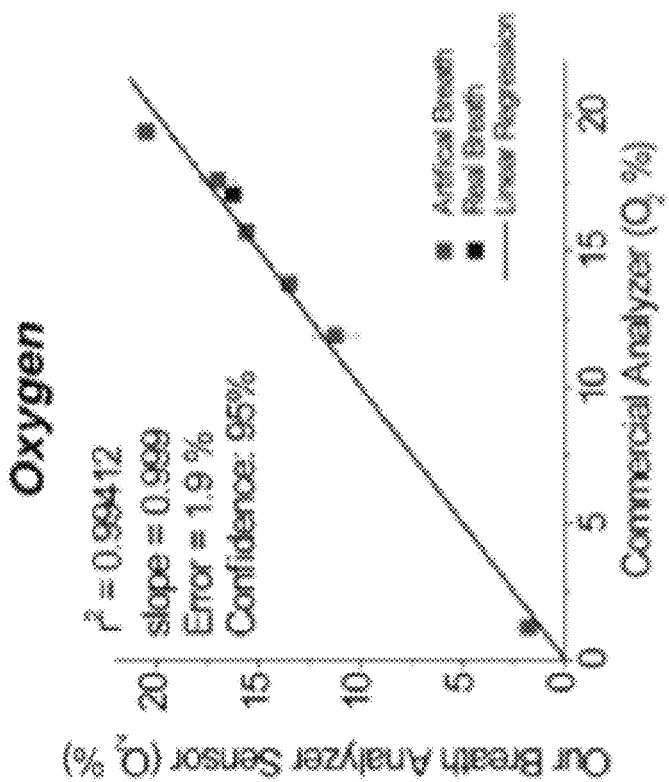
FIG. 5A graphically shows an example of detection of oxygen with a microporous membrane sensor in artificial and real breath samples and correlation of the membrane sensor results with results assessed from an electrochemical oxygen analyzer.

Referring now to FIG. 5A, there shown is a linear regression plot comparing oxygen detection by a metabolic analyzer as disclosed herein on the Y axis vs. a commercial oxygen sensor along the X axis of the plot. Detection of oxygen from artificial and real breath samples was demonstrated in the porous membrane sensor, by using off-line and on-line sample collection modes. As shown by plot 25, the performance of the sensor has allowed discrimination of samples with 0.3% oxygen content difference within clinical relevant levels of 15-20% oxygen.

Acetone Detection with Porous Membrane Sensor

Referring now to FIG. 5B, there shown is a linear regression plot comparing acetone absorbance and equivalent acetone concentration using porous membranes embedded with molecular probes for acetone. In this example, porous membranes embedded with molecular probes for acetone were tested using cell phone cameras. A test was performed with acetone solutions containing part-per-billion (ppb) equivalent levels and color detection was carried out with a cell phone camera. Absorbance readings from a sensing composite material based on salicylic aldehyde embedded in an alkaline catalyst were plotted. As shown by plot 30 membranes have demonstrated capability of detection of acetone at ppb equivalent levels.

Integration of the Membrane Sensor in a Cell Phone

Referring now to FIG. 6, a process for using a metabolic analyzer incorporated into a cellular telephone is schematically shown. The integration of the porous membrane sensor in a cell phone 6 has been carried out to demonstrate the concept of the metabolic analyzer for non-invasive and sustainable clinical condition monitoring and assessment. The sensor 3 has been integrated in a single device (mouthpiece) including a battery powered LED. The integrated device has been attached to a cell phone 6 that detects and quantifies consumed oxygen and produced carbon dioxide from breath obtained with a fixed volume in a timed period.

The cell phone 6 has a specific application that allows hybrid sensor images collection before and after breathing, signal processing to determine color change on the hybrid sensor, and storage of data and other relevant diet patient's information. The specific application may comprise a software application, which may be generated using conventionally available programming techniques available to those skilled in the art having the benefit of this disclosure. In addition, the cell phone also can send the information wirelessly, and enable the evaluation of the breath analytes patterns by the professionals, who can provide feedback to the patient.

In one example of a process using the metabolic analyzer, the metabolic analyzer is connected to the cell phone before breathing in step 1. The sensor exhibits characteristic colors for the $O_2$ sensing, reference and $CO_2$ sections. A plastic bag 50 is in fluid communication with the mouthpiece. During the second step the metabolic analyzer is disconnected from the cell phone and a user breathes into the analyzer with the exhaled breath being captured in the plastic bag. In step 3 the unit is again coupled to the cell phone and the breath sample captured in the plastic bag is analyzed. The $O_2$ sensing and $CO_2$ sections will register a color change for assessing the sample for those analytes.

Referring now to FIG. 6', an alternative process for using a metabolic analyzer incorporated into a cellular telephone is schematically shown. Here a solid support sensor 601 is incorporated into an assembly 605 including a cell phone 6 and a mouthpiece 610. In use the subject breaths into the mouthpiece and a set of sensors 60, 62 senses $O_2$ and $CO_2$ respectively. Reference character 54 shows the $O_2$ sensor prior to breathing and reference 60 shows the change in color characteristics after breathing. Note that in this configuration no bag is needed as the solid support sensor is simply inserted into the assembly 605 in a port 606 provided for that purpose.

Anticipated Fields of Application

As mentioned before, the capability of detection of carbon dioxide and oxygen in breath allows determining the energy expenditure of a subject via indirect calorimetry approach. In addition the detection of other breath components such as acetone allows diagnosis of lipid metabolism. The present application is of relevance for metabolic evaluation of subject under particular nutrition and physical activities regimes. In addition, applications of the analyzer can be found in the diagnosis and management of respiratory diseases such as asthma, chronic obstructive pulmonary disease (COPD), fibrosis cystic, and other respiratory diseases via evaluation of breath-by-breath carbon dioxide concentration level (so-called capnography), and liver or kidney-malfunctions via detection of other metabolites such as hydrogen sulfide, and ammonia. Although the proposed approach for metabolic analyzers is versatile and works in different kind of environments, suitable implementation scenarios include point-of-care and home-based healthcare applications.

Methods Involving Using a Metabolic Analyzer for Weight and Fitness Applications Having described the apparatus of the present disclosure, now presented are application methods using a metabolic analyzer described above for weight and fitness management. The metabolic analyzer allows for indirect calorimetry that detects breath biomarkers and quantifies a person's energy expenditure (kcal/day) and metabolized food substrate. Such capabilities can benefit the large and growing obese and overweight population, and also provide more effective training of athletes and armed forces. Unlike physical activity monitoring devices, such as accelerometers, which cannot monitor resting energy expenditures, the indirect calorimeter in the prior application targets specifically energy expenditure at resting states. This is important because over 75% of a person's energy expenditure is resting energy.

As also disclosed above, additional breath biomarkers can be detected as additional metabolic signatures. One example is acetone, indicator of fat burning rate. The energy expenditure, together with acetone detection capability, provides additional values for more effective weight loss and control, and physical training programs.

Preliminary Results

In order further demonstrate the accuracy of the presented metabolic analyzer, as well as its friendly usability, and utility for weight and fitness management plans the following results are presented.

Analytical Validation of the Metabolic Analyzer

As stated above, the metabolic analyzer is easy-to-use by non-experts in the field of metabolic assessment (e.g. nutritionist, dietitian, nurses, health professionals, exercise physiologist). Non-experts in the field of weight and fitness management field have used it, and the results have been compared with the reference method, using Douglas bags. A total of 15 subjects have been used to perform the comparisons. The Douglas bag method collects breath sample with a bag for a given time period, and analyzes the amounts of consumed $O_2$, and produced $CO_2$ using paramagnetic resonance/electrochemistry, and infrared[22] detection techniques, respectively. Based on the measured $O_2$ and $CO_2$, it then determines REE.

Now referring to FIGS. 7A-D that show correlation results of: (A) oxygen consumption rate (VO2), (B) carbon dioxide production rate (VCO2), and REE (C) from ASU metabolic analyzer vs. Douglas bag method, and (D) Bland-Altman plot for REE measures performed with the new metabolic analyzer as disclosed herein vs. a Douglas Bag Method. Referring specifically to FIG. 7 C, the correlation plot slope close to 1, and the regression coefficients >0.95 demonstrate the high accuracy of the analyzer. Referring specifically to plot 7D, the random differences of readings in this Bland-Altman plot indicate unbiased readings with REE increase, as well as REE reading errors between 1-6% (95% CI), which is performance favorably comparable to commercial metabolic carts typically used in clinical settings. The precision and repeatability have also been tested and analyzed using breath samples from individuals with stabilized diets and lifestyles (exercise), e.g., between runs during the same day, and between runs during different days.[24] These tests have shown that the relative errors of the metabolic analyzer for REE are smaller than 2%.

Clinical Validation Studies

Figure 2B:
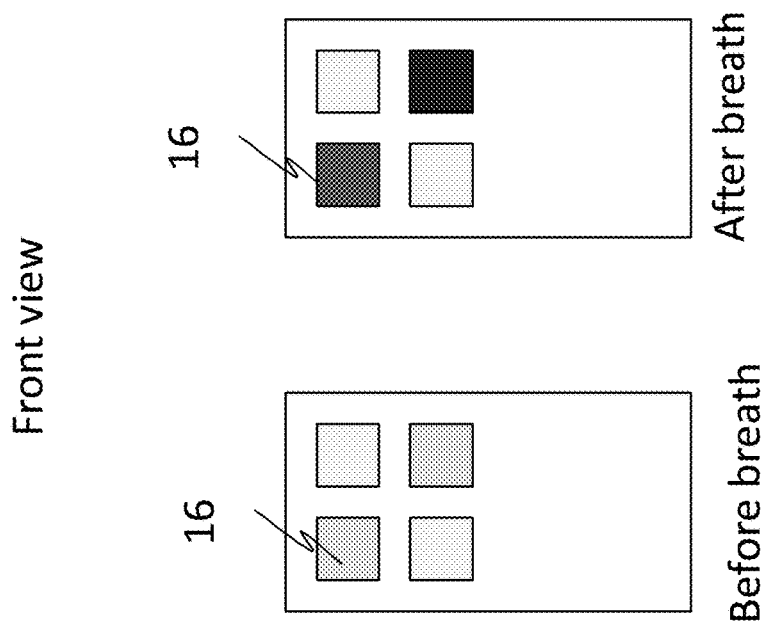
Figure 2A:
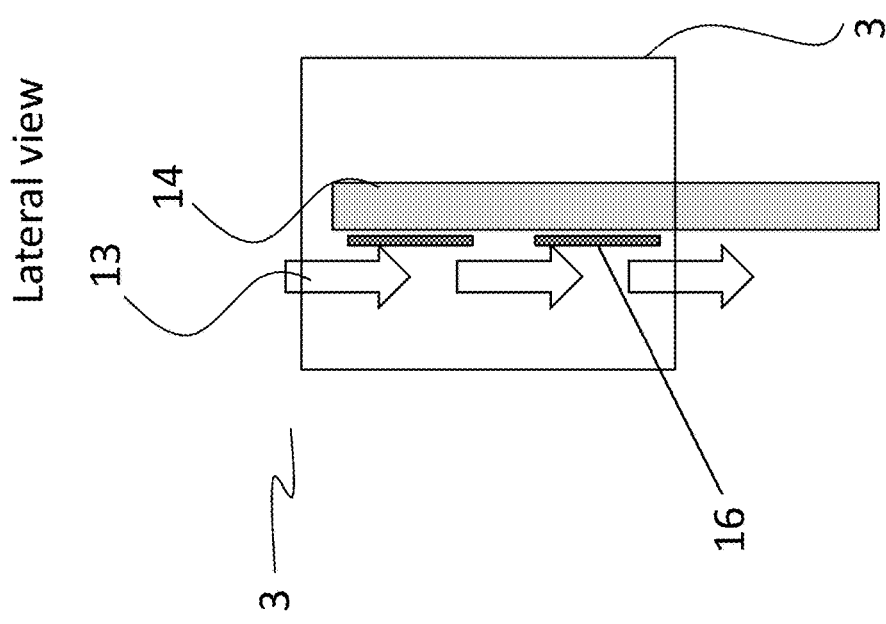

Referring now to FIGS. 8A-8A2 there shown are plots of a cross-sectional study performed with the metabolic analyzer including REE trends with physical parameters of (A) weight, (A1) lean body mass, and (A2) muscular mass. Small pilot studies have been carried out by measuring REE with the metabolic analyzer, which performs on-line real-time analysis (FIG. 8A1), with off-line reference method (Douglas Bag) and on-line breath-by-breath methods (by Oxycon® Mobile, and metabolic carts). The REE and RQ readings from the metabolic analyzer compared to both off- and on-line methods are in excellent agreement with the reference methods (>90% with regression coefficients larger than 0.95).[24] In addition, REE values measured with the metabolic analyzer correlate well (>90%) with physical parameters, such as weight, lean body mass, and muscular mass (FIG. 8A2). In parallel, individuals engaged in different physical activities and diets have also been tested,[25,26] and results support weight and fitness intervention strategies (see below).

Physical Activities Tests:

Referring now to FIGS. 8B-8B2 there shown are plots representing energy expenditure change with physical activity including (B) increased load in a treadmill, (B2) corresponding REE and EE rate curve and (B2) lactate curve, indicating lactate threshold, determined by $VO_2$ measures. The value of blood lactate threshold (2.5 mM) matches the literature values, and indicates the capability of $VO_2$ to determine anaerobic metabolic conditions, under physical activities. The above results represent physical activities tests conducted in order to evaluate the metabolic analyzer's sensitivity to detect changes in the metabolic rate of an individual. REE and Energy Expenditure Rate (EE), and RQ were measured with the study subjects at resting state, and engaged in physical activity (treadmill) with increasing load. The subjects were asked to provide breath samples at the end of each session of physical activity with increased speed or/and slope. As expected, the EE and RQ values determined by the metabolic analyzer increased with the load. Furthermore, oxygen consumption rates ($VO_2$) measured in parallel allowed accurate determination of lactate concentration threshold, an important quantity that identifies anaerobic metabolic stage of individuals under physical activities (FIG. 8B2). These tests show that the metabolic analyzer can accurately detect the change of an individual's metabolic rate.

Diet Tests:

Referring now to FIGS. 9A and 9B there shown are REE and weight profiles of subject under a weight maintenance plan, and weight reduction intervention plan respectively. To evaluate the metabolic analyzer's capability to detect metabolic changes associated with dietary modifications, longitudinal pilot studies of individuals during weight loss diet have been carried out and compared with those who are on weight maintenance diet. For subjects with well-balanced caloric intake and energy expenditure rate (e.g. daily calorie intake equals to daily total energy expenditure), REE fluctuations were found to be 2%, and associated to small weight fluctuations of ~0.2% (FIG. 9B). On the contrary, for subjects following a dietary regimen (e.g. weight loss plan), the changes of REE were more evident, and correlated well with specific interventions. Arrows 90 show intervention events with physical activity recommendations. For instance, we have observed that changes in REE and weight in intervention cases at least doubles the changes found in non-intervention cases. Therefore, an REE profile is a "silent witness" to metabolic variations, thus allowing for changes in habits to be detected so that corrective actions to the individuals' weight management plan can be made. In addition, we have observed that REE values are important for the determination of weight normalized metabolic rate (REE/Kg), which may allow detection of particular metabolic conditions, such as those resulting from hormone abnormalities (e.g. hypo or hyperthyroidism), which may prove useful for disease identification and management (not shown).

Example of Method of Use for Weight and Fitness Management

REE, and body weight profiles, as well as RQ profiles can be analyzed case by case, and compared with recommended intervention inputs to determine the individual's personal metabolic features or non-adherence issues. Here, we present an example of the method of use for our metabolic analyzer.

Initial Stage:

Referring now to FIG. 10, there shown is an expected scenario from weight (WT) management in obese or overweight subjects. A subject can measure his/her metabolic data (REE, RQ, and weight) every week. When the metabolic analyzer is used in the first time, the subject can enter his/her personal information (date of birth, height, physical dimensions (hip, waist), ethnicity, gender), and weekly work, home, and recreational physical activities. Then the subject can perform the first REE, RQ, and weight measurements. In addition to these data, the analyzer estimates TEE from the measured REE, and recorded physical activities (type and frequency) using METs database.[27,28]

Based on the initial REE and TEE measures, the analyzer can recommend an initial calorie intake. If the subject has a normal body mass index (BMI), the recommended calorie intake is equal to TEE. If the subject has an overweight or obese BMI, the recommendation can follow, for instance, the American Dietitian Association's (ADA's) guideline,[29] which recommends a decrease of 500 kcal/day in the dietary intake[29] (FIG. 10, week 1) or a decrease of 250 kcal/day in the dietary intake and physical activity equivalent to 250 kcal/day. In addition, the analyzer can also recommend how many minutes of a given activity the subject will need to meet the calories reduction target. Note that since the individual's REE is known, the right amount of a particular physical activity based on the specific subject's metabolic rate (kcal/day), using the MET tables.[27]

The procedure described above is for adults. In case of children and teenagers, similar procedure can be followed but recommendations of calorie decrease or activity energy expenditure could be adjusted for this population following pediatric ADA recommendations.[39]

Later Stages:

After the first recommendation in week 1, follow-up recommendations will be based on the changes of REE, TEE, and weight (WT). These changes can likely vary from subject to subject, and also from time to time, leading to different scenarios. One likely scenario is illustrated in FIG. 10. In week 2, the subject experiences WT loss (WT2<WT1), but maintain the same REE (REE2=REE1). Since the REE does not change, same amounts of food intake and physical activity are recommended until new evidence is found in the following weeks. For instance, in week 3, the subject reports a REE decrease (REE3<REE2), but no weight loss (WT3=WT2). In this case, the decrease in the REE indicates that the subject's metabolic rate has decreased. This is a common and neglected situation in weight loss plans[31-35] that typically lead to unsuccessful weight and fitness management. In order to lose weight, the subject must increase his/her REE or further reduce food intake. The most effective way to increase REE is through physical activity.[36-38] The analyzer can recommend the subject to perform physical activity (e.g. brisk walking or similar), and slightly further decrease her/his calorie intake (see output week 3). If REE increases in week 4 (i.e., REE4>REE3), and the weight decreases (WT4<WT3), then the goal of weight loss is achieved. The subject is asked to maintain the food intake and physical activity levels until a desired BMI is reached. Many other scenarios may also occur. In any case, the analyzer includes a routine of recommendations considering the 9 different options resulting from changes in REE and weight greater, equal or smaller than 0 to assist the subject to manage her/his weight or fitness. If metabolic rate decreases with the intervention, this would be considered unsuccessful since maintaining weight loss solely by lowering calorie intake would unlikely be a long-term strategy, and may even lead to undesired health consequences.[39]

The unique power of the method that the recommendations are personalized based on accurate and timely energy expenditure and weight data for each individual, and thus increasing the chance of success.[40] This is in sharp contrast to many current overweight and obesity management programs that involve the use of equations to estimate REE.[27] The equations are unreliable.[42] In addition, the disclosed method does not require assistance from a dietitian, nutritionist, or a health care professional.

Referring now to FIG. 11, a high level flow chart of an example of a method for weight and/or fitness management is schematically shown. In one example the method is carried out by using a metabolic analyzer that measures both oxygen and carbon dioxide 100. The metabolic analyzer is substantially as described above including a plurality of integrated collection-detection sensors with for high efficiency and collection, high specificity and simultaneous detection of metabolic signatures, including at least oxygen and carbon dioxide, in breath via a porous membrane with high density of sensing binding sites, wherein the porous membrane includes sensing materials such that the sensing binding sites are specific to the metabolic signatures, and change colors upon interactions with the metabolic signatures. Another process step includes measuring weight of the subject using a weight measurement device 102. Another process step includes recommending food intake and/or physical activity based on at least the readings of the metabolic analyzer and weight of the subject 104.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

1—Oxycon Mobile, commercial metabolic analyzer from Viasys Healthcare, viasyshealthcare.com.
2—Lynette Ross; Drik Fengels; Edwin M. Pearce, Jr.; James R. Mault; Christopher L. Sandys; Tom Kilbourn; Respiratory analyzer for exercise use; U.S. Pat. No. 7,108,659 B2, Date of patent: Sep. 19, 2006
3—C. Peter Howard; Joel Grimes; Metabolic analyzer transducer; Patent No. US 2009/0227887, Date of patent: Sep. 10, 2009
4-Ming-Hsiung Yeh; Sensor formulation for simultaneously monitoring at least two components of a gas composition; U.S. Pat. No. 6,989,246 B2, Date of patent: Jan. 24, 2006
5—Kemeta, Acetone breath analyzer, kemeta.com.
6—Paul E. Cranley, Jeffrey R Allen, Kristine L. Danowski, James A McIntyre, Theodore E Miller Jr, Bettina M Rosner, Alan D Strickland, Venkiteswaran Subramanian, Larry Sun; Enzyme-based system and sensor for measuring acetone; Patent No. US2005/0084921 A1; Apr. 21, 2005
7—Jeffrey R Allen, Paul E. Cranley, Kristine L. Danowski, James A McIntyre, Reed A. Shick, Bettina M Rosner, Larry Sun; Medical apparatus for breath detection; Patent No. US2008/004542 A1; Jan. 3, 2008
8—Siemmens, Acetone breath analyzer under development, siemens.com.
9—M. Fleischer, et. al., FET-based sensor for detecting reducing gases or alcohol and associated production and operation method, Patent, No. US2009/0127100 A1, 2008
10—Chuan-Jian Zhong, Lingyan Wang, Susan Lu, Xiajing Shi, Weibing Hao, Jin Luo; Multi-modulated nanoparticle-structured sensing array and pattern recognition device for detection of acetone in breath; Patent No. US2009/0049890 A1, Feb. 26, 2009
11—Barbara Landini; Joan K. Vrtis; Roberta Druyor-Sanchez; Shane Bravard; David Luttroll, James A. Mcintryre; Paul E. Cranley; Breath delivery system and method; International Publication No. WO 2009/058366 A1.
12—James Montagnino; Metabolic fitness training apparatus; Patent No. US 2002/0143267 A1, Oct. 3, 2002.
13—Yixiang Duan, Wenqing Cao; Apparatus and method for monitoring breath acetone and diabetic diagnostics; Patent No. US2007/0229818 A1; Oct. 4, 2007.
14—McArdle, W. D., Katch, F. I. & Katch, V. L. Exercise Physiology: Energy, Nutrition, & Human Performance. *Lippincott Williams & Wilkins* (2007).
15—Chang, R. Weight Management System. Patent Application Publication, US2006/0259323 A1 (Nov. 16, 2006).
16—Karkanen, K. M. Integrated weight loss control method. U.S. Pat. No. 5,839,901 (Nov. 24, 1998).
17—Bodlaender, M. P., Nicolaas, A. R., Schneider, O. & Simons-Nikolova, M. Weight management system using adaptive targets. PCT WO 2007/072395 A2/A3 (28 Jun. 2007).
18—Thompson, E. S. Method and process for weight management. Patent Application Publication, US2009/0131814 A1 (May 21, 2009).
19—Mault, J. R. Integrated calorie management system. U.S. Pat. No. 6,478,736 B1 (Nov. 12, 2002).
20—Tsang, P. T. S. K. Method for weight management. Patent Application Publication, US2011/0143322 A1 (Jun. 16, 2011).
21—Edman, C. F., Bhavaraju, N. C. & Drinan, D. D. Metabolic energy monitoring system. Patent Application Publication, US2010/0049004 A1 (Feb. 25, 2010).
22—Oxycon Pro Instrument: reference methods for oxygen (paramagnetic) and carbon dioxide (infrared) viasyshealthcare.com.
23—Kaplan, A. K. & Pesce, A. J. E. Clinical Chemistry: Theory, Analysis, Correlation. Mosby, Inc. (1989).
24—Kaplan, L. A. & Pesce, A. J. Clinical Chemsitry: theory, analysis, and correlation. Mosby, Co, St. Louis, Toronto, Princeton (1984).
25—Watson, D. et al. Effects of continuous vs fractionalized exercise on caloric expenditure in non obese males and females. Medicine and Science in Sports and Exercise 34, S217 (2002).
26—Watson-Winfield, D. et al. Continuous vs fractionalized exercise on caloric expenditure in non-obese and obese females. Medicine & Science in Sports & Exercise 35, S106 (2003).
27—Ainsworth, B. E. et al. COMPENDIUM OF PHYSICAL ACTIVITIES—CLASSIFICATION OF ENERGY COSTS OF HUMAN PHYSICAL ACTIVITIES. Medicine And Science In Sports And Exercise 25, 71-80 (1993).
28—Ainsworth, B. E. et al. Compendium of Physical Activities: an update of activity codes and MET intensities. Medicine And Science In Sports And Exercise 32, S498-S516 (2000).
29—Adult weight management evidence-based nutrition practice guideline. American Dietetic Association, guidelines.gov, US Department of Health and Human Services.
30—Pediatric weight management evidence-based nutrition practice guideline. American Dietetic Association, US Department of Health and Human Services, guidelines.gov.
31—Elliot, D. L., Goldberg, L., Kuehl, K. S. & Bennett, W. M. SUSTAINED DECREMENT IN RESTING METABOLIC-RATE FOLLOWING WEIGHT-LOSS. Clinical Research 35, A365-A365 (1987).
32—Elliot, D. L., Goldberg, L., Kuehl, K. S. & Bennett, W. M. SUSTAINED DEPRESSION OF THE RESTING METABOLIC-RATE AFTER MASSIVE WEIGHT-LOSS. American Journal Of Clinical Nutrition 49, 93-96 (1989).
33—Heshka, S., Yang, M. U., Wang, J., Burt, P. & Pisunyer, F. X. WEIGHT-LOSS AND CHANGE IN RESTING METABOLIC-RATE. American Journal Of Clinical Nutrition 52, 981-986 (1990).
34—Leibel, R. L., Rosenbaum, M. & Hirsch, J. CHANGES IN ENERGY-EXPENDITURE RESULTING FROM ALTERED BODY-WEIGHT. New England Journal of Medicine-332, 621-628 (1995).
35—Rosenbaum, M., Kissileff, H. R., Mayer, L. E. S., Hirsch, J. & Leibel, R. L. Energy intake in weight-reduced humans. Brain Research 1350, 95-102, doi:10.1016/j.brainres.2010.05.062 (2010).
36—Boileau, R. & Horswill, C. Body Composition in Sports: Measurement and Applications for Weight Loss and Gain. In: Exercise and Sports Science Edited by W E Garrett, D T Kirkendall. pp. 319-338. Philadelphia, Pa.: Lipincott Williams & Wilkins; 2000: 319-338.
37—Hansen, D., Dendale, P., Berger, J., van Loon, L. J. C. & Meeusen, R. The effects of exercise training on fat-mass loss in obese patients during energy intake restriction. Sports Med. 37, 31-46 (2007).
38—King, N. A. et al. Metabolic and behavioral compensatory responses to exercise interventions: Barriers to weight loss. Obesity 15, 1373-1383 (2007).
39—Thomas, T. R. et al. Exercise and the metabolic syndrome with weight regain. Journal of Applied Physiology 109, 3-10, doi:10.1152/japplphysiol.01361.2009 (2010).
40—Jones, V. Resting Metabolic Rate: A Critical, Primary Care Screening Test. MedGenMed, accessed via ncbi.nlm.nih.gov, 76 (2006).
42—Horie, L. M., Gonzalez, M. C., Torrinhas, R. S., Cecconello, I. & Waitzberg, D. L. New Specific Equation to Estimate Resting Energy Expenditure in Severely Obese Patients. Obesity 19, 1090-1094, doi:10.1038/oby.2010.326 (2011).

What is claimed is:

1. A method for metabolic analysis of a subject comprising:
providing a solid support or porous membrane including a plurality of sensing binding sites;
selecting an array of sensing materials where each sensing material is capable of reacting with a specific analyte so that when operating together at least two different metabolic signatures can be sensed and wherein each sensing material changes absorbance upon interactions with its specific analyte;

affixing the array of sensing materials to the plurality of sensing binding sites;

affixing at least one reference area to the plurality of sensing binding sites, where the at least one reference area is insensitive to the analytes to allow corrections and noise removal;

illuminating the plurality of sensing binding sites with at least one light source providing incident light;

operating at least one light detector for simultaneously collecting and detecting a first plurality of non-fluorescence initiated color change signals from the plurality of sensing binding sites at an absorbance wavelength, wherein the first plurality of non-fluorescence initiated color change signals consists of a first change of light intensity of the incident light transmitted through or reflected from the solid support, collected at the absorbance wavelength, and includes characteristic colors for oxygen, and carbon dioxide, and the at least one reference area;

introducing a flow of gases to the plurality of sensing binding sites;

operating the at least one light detector for simultaneously collecting and detecting a second plurality of non-fluorescence initiated color change signals from the plurality of sensing binding sites when exposed to the flow of gases, wherein the second plurality of non-fluorescence initiated color change signals consists of a second change of light intensity at the absorbance wavelength transmitted through or reflected from the solid support;

comparing the first plurality of non-fluorescence initiated color change signals to the second plurality of non-fluorescence initiated color change signals to generate a plurality of registered non-fluorescence initiated color changes;

processing the plurality of registered non-fluorescence initiated color changes to determine the changes in oxygen concentration and carbon dioxide concentration; and determining the at least two different metabolic signatures from the changes in oxygen concentration and carbon dioxide concentration.

2. The method of claim 1 further comprising processing the at least two different metabolic signatures for measuring resting energy expenditure (REE), and respiratory quotient (RQ).

3. The method of claim 2 wherein recommendations for diet and exercise goals are produced on changes of REE and RQ.

4. The method of claim 1 further comprising processing the at least two different metabolic signatures to measure ketones, sulfur compounds, ammonia and water.

5. The method of claim 1 further comprising:

wherein the act of introducing a flow of gases to the plurality of sensing binding sites consists of introducing breath to flow over the array of sensing materials through a mouthpiece attached to the solid support or porous membrane; and monitoring breath volume or rate from the mouthpiece.

6. The method of claim 1 wherein the at least one light detector includes a photodetector, complementary metal oxide semiconductor (CMOS), or a charge-coupled device (CCD).

7. The method of claim 5 wherein monitoring breath volume or rate comprises operating a flow meter or a pressure sensor from which the breath volume or rate is determined.

8. The method of claim 5 wherein monitoring breath volume or rate comprises coupling a bag with a fixed volume to an outlet of the mouthpiece to collect a breath after passing it over the sensing materials in a timed period.

9. The method of claim 1 further comprising operating a mobile device to carry out the acts of comparing the first plurality of color change signals to the second plurality of color change signals to generate a plurality of registered color changes, determining the change in oxygen concentration and carbon dioxide concentration responsively to the plurality of registered color changes; and determining the at least two different metabolic signatures from the change in oxygen concentration and carbon dioxide concentration.

10. The method of claim 5 further comprising locating the plurality of sensing binding sites on the mouthpiece.

11. The method of claim 5 further comprising locating the at least one light source and the at least one light sensor at opposite sides of the array of sensing materials.

12. The method of claim 5 further comprising locating the at least one light source and the at least one light sensor on the same side relative to the solid support or porous membrane.

13. The method of claim 5 further comprising wirelessly transmitting signals from the at least one light sensor.

14. The method of claim 5 further comprising integrating the mouthpiece, the at least one light source, the array of sensing materials and the at least one light sensor into a unitary device.

15. The method of claim 1 wherein the array of sensing materials comprises nanoparticles or micro particles.

16. The method of claim 1 wherein the solid support comprises a material selected from a group consisting of synthetic polymers, natural polymers, polyester, nylon, cellulose, glass-produced substrates, fiber glass, sol gel, silica, alumina, silica gel and composites of the materials listed in the group.

17. The method of claim 14 further comprising monitoring metabolic processes including: integrating the unitary device in a cell phone; and using the unitary device as a metabolic analyzer for detecting consumed oxygen rate and produced carbon dioxide rate from breath obtained with a fixed volume in a timed period.

* * * * *